(12) United States Patent
Arribas Lopez et al.

(10) Patent No.: US 8,741,586 B2
(45) Date of Patent: Jun. 3, 2014

(54) ANTIBODIES AGAINST HER2 TRUNCATED VARIANT CTF-611

(75) Inventors: Joaquin Arribas Lopez, Cerdanyola del Valles (ES); Kim Pedersen, Barcelona (ES); Pier-Davide Angellini, Barcelona (ES); Josep Lluis Parra Palau, Barcelona (ES); Jose Baselga Torres, Barcelona (ES)

(73) Assignees: Fundacio Privada Institucio Catalana de Recerca i Estudis Avancats, Barcelona (ES); Fundacio Privada Institut d'Investigacio Oncologica de vall d'Hebron, Barcelona (ES)

( * ) Notice: Subject to any disclaimer, the term of this patent is extended or adjusted under 35 U.S.C. 154(b) by 415 days.

(21) Appl. No.: 12/961,004

(22) Filed: Dec. 6, 2010

(65) Prior Publication Data

US 2011/0135653 A1 Jun. 9, 2011

(30) Foreign Application Priority Data

Dec. 7, 2009 (EP) .................................. 09380183

(51) Int. Cl.
*C12P 21/08* (2006.01)
*C07K 16/30* (2006.01)
*C07K 16/28* (2006.01)
*G01N 33/574* (2006.01)
*G01N 33/573* (2006.01)
*G01N 33/567* (2006.01)
*G01N 33/50* (2006.01)

(52) U.S. Cl.
USPC ........... 435/7.23; 435/7.1; 435/7.2; 435/7.21; 435/7.9; 435/7.92; 435/70.1; 435/70.2; 435/70.21; 435/326; 435/330; 435/334; 435/344; 435/344.1; 436/501; 436/503; 436/518; 436/548; 436/63; 436/64; 530/387.1; 530/387.3; 530/387.7; 530/388.1; 530/388.22; 530/388.8; 530/388.85; 530/391.1; 530/808; 530/809; 530/866; 424/130.1; 424/135.1; 424/138.1; 424/141.1; 424/143.1; 424/155.1; 424/156.1

(58) Field of Classification Search
USPC ........ 530/387.1, 387.3, 388.1, 388.22, 388.8, 530/388.85, 391.1, 808, 809, 866; 424/130.1, 135.1, 138.1, 141.1, 143.1, 424/155.1, 156.1; 435/70.1, 70.2, 70.21, 435/326, 330, 334, 344, 344.1, 7.1, 7.2, 435/7.21, 7.23, 7.9, 7.92; 436/501, 503, 436/518, 548, 63, 64

See application file for complete search history.

(56) References Cited

U.S. PATENT DOCUMENTS

2009/0311262 A1    12/2009   Arribas Lopez et al.
2010/0143927 A1*   6/2010    Sperinde et al. ............... 435/6

FOREIGN PATENT DOCUMENTS

WO    89/06692       7/1989
WO    2010/000565    1/2010

OTHER PUBLICATIONS

Anido et al., EMBO J., 25:3234-3244 (2006).
Molina et al., Clin. Cancer Res., 8:347-353 (2002).
Pedersen et al., Mol. Cell. Biol., 29(12):3319-3331 (2009).
Saez et al., Clin. Cancer Res., 12:424-431 (2006).
Scaltriti et al., J. Natl. Cancer Inst., 99:628-638 (2007).

* cited by examiner

*Primary Examiner* — Ram R Shukla
*Assistant Examiner* — Anne Holleran
(74) *Attorney, Agent, or Firm* — McAndrews, Held & Malloy

(57) ABSTRACT

The present invention relates to a method of diagnosis and therapy of cancers expressing the HER2 receptor.

The invention provides antibodies or fragments thereof that recognise an epitope of the HER2 receptor truncated form CTF-611, said epitope being defined by a sequence included in SEQ ID NO: 2, and that are capable of discriminating between CTF-611 and CTF-616 (represented by SEQ ID NO:7), preferably additionally capable of discriminating between CTF-611 and CTF-613 (represented by SEQ ID NO:6).

The invention also provides a method of cancer diagnosis using the disclosed antibodies, which comprises the detection of the presence of the HER2 receptor truncated form consisting of the amino acid sequence SEQ ID NO: 1 in a patient sample.

10 Claims, 8 Drawing Sheets

ANTIBODIES AGAINST HER2 TRUNCATED VARIANT CTF-611

The present application is filed as a U.S. patent application of European Patent Application No. 09380183.5, which was filed Dec. 7, 2009. The entire text of the aforementioned application is incorporated herein by reference in its entirety.

The present invention relates to a method of diagnosis in isolated samples of cancers expressing the truncated variant CTF-611 of the HER2 receptor. The invention also provides compounds for use in the early diagnosis and identification of the cancer as well as for use in therapy.

BACKGROUND ART

HER2 (also known as c-erbB2, ErbB2 or Neu) is a type I transmembrane protein belonging to the family of epidermal growth factor receptors or EGFR, also known as HER1 or ErbB1. Two additional members, HER3 and HER4 complete this family. When HER1, 3 or 4 binds to an EGF-type ligand, its extracellular domain adopts the conformation referred to as "open", which allows the formation of homodimers and heterodimers. Even if it does not bind to any ligand, HER2 also interacts with other HER receptors linked to a ligand, due to the fact that its extracellular domain is constitutively in "open" conformation.

The dimerisation directed by the extracellular domain leads to interaction of the intracellular kinase of HER receptors and to the subsequent transphosphorylation of some tyrosine residues. These phosphotyrosines act as couplers of a group of intracellular phosphotyrosine-binding proteins. The interactions established at the plasma membrane are transduced to the cell nucleus by means of different signalling routes, such as the protein kinase route activated by mitogen activated protein kinase (MAPK), the protein kinase route activated by stress (JNK), phospholipase C gamma, etc. All of these signalling circuits control the expression of genes that act in a coordinated way to modify determining aspects of the state of the cell, such as cell proliferation, migration, survival and adhesion. Thus, depending on the cell context, activation of the HER receptors results in a dramatic cell response, which can range from transformation into a malignant cell to a premature senescence.

In human breast tumours, a series of carboxy terminal fragments or CTFs has been often found, which are assumed to include the transmembrane and cytoplasmic domains of HER2. (Molina et al, "NH(2)-terminal truncated HER2 protein but not full-length receptor is associated with nodal metastasis in human breast cancer", *Clinical Cancer Research*-2002, Vol. 8, pp. 347-353). It is also known that patients with breast cancer expressing the HER2 CTFs, or what comes to be the same truncated forms which do not include the N-terminal end of HER2 (HER2 CTFs), have a greater probability of developing metastasis (Molina et al. 2002-supra) and a worse prognosis than those patients who mainly express the complete form of HER2 (Saez et al., "p95HER2 predicts worse outcome in patients with HER2-positive breast cancer", *Clinical Cancer Research*-2006, Vol. 12, pp. 424-431).

Therefore, it is very important to be able to detect the presence of HER2 in tumours on time and even more to determine whether it is in a complete or truncated (CTF) form.

Nowadays, at the level of routine clinical tests antibodies are used to detect the presence of the complete form of HER2, in order to determine the type of breast tumour in question. In the event of detecting the presence of HER2, the recommended therapy consists of administering therapeutic monoclonal antibodies, such as Genentech's trastuzumab. The use of this monoclonal antibody for the treatment of cancer is described in the application WO 8906692 on behalf of Genentech. WO 8906692 describes monoclonal or polyclonal antibodies directed against the extracellular region of HER2, this extracellular region matching with the complete external part of the protein, which is its N-terminal end. As previously mentioned, the epitopes recognised by the antibodies cited in WO 8906692 are antigenic regions of the extracellular domain of the HER2 complete form and are not included in truncated forms or carboxy-terminal fragments of HER2. Therefore, with the antibodies and the diagnosis method described in WO 8906692 it will not be possible to detect the presence of truncated HER2 (CTFs). Also, in breast tumours where said CTFs of HER2 are expressed, antibodies such as trastuzumab are not therapeutic, since they do not recognise any epitope. This fact explains the resistance to the treatment with trastuzumab observed in patients expressing truncated forms (CTFs) of HER2.

Patients who express truncated forms or CTFs of HER2 should be treated with alternative therapies in order to prevent the poor prognosis numbers observed by Saez et al 2006 (supra). For the purpose of detecting (diagnosing) and treating as soon as possible people having tumours where HER2 truncated forms are expressed, it is very interesting to be able to distinguish what form of HER2 is expressed in order to act in consequence.

The document of Anido et al., "Biosynthesis of tumorigenic HER2 C-terminal fragments by alternative initiation of translation", *European Molecular Biology Organization (EMBO) Journal*-2006, Vol. 25, pp. 3234-3244, describes that in addition to the fragment generated by the action of the alpha-secretases on the HER2, which gives rise to a truncated form (CTF) known as P95 that includes the transmembrane and cytoplasmic fragment of the receptor, two truncated forms (CTF) are also generated through a mechanism of alternative initiation of translation starting from two methionines located upstream and downstream, respectively, of the transmembrane domain of HER2. Specifically, the methionines for the alternative initiation of translation correspond to methionine 611 and methionine 687 of the amino acid sequence with access number M11730.1 of the UniGene database of the National Center for Biotechnology Information (NCBI). This document also shows that these alternative forms of the HER2 receptor (CTFs) are present in breast tumours. In particular, it indicates that the most abundant corresponds to the form known as CTF687, or in other words, to the protein obtained by the alternative initiation of translation starting from the methionine in position 687. Anido et al. proposes as therapy the use of inhibitors of the tyrosin kinase activity of HER2, such as lapatinib, in order to minimise the growth of the tumours expressing these truncated forms of HER2. The inhibitors of tyrosine kinases act by interacting with the C-terminal end of the HER2 receptor that is present in an integral manner in both the complete receptor and in the CTFs derived from it or produced by alternative initiation of the translation.

The document of Scaltriti et al, "Expression of p95HER2, a truncated form of the HER2 Receptor, and response to anti-HER2 therapies in breast cancer", *Journal of National Cancer Institute*-2007, Vol. 99, pp. 628-368, represents an example of a study into an alternative methodology for detecting the presence of one of the HER2 receptor truncated forms and lists some of the possible causes of resistance to the treatment with trastuzumab (Herceptin). In particular, it emphasises the accumulation of the p95HER2 fragment (product of the proteolysis of HER2 by alpha-secretases) and other truncated forms of the receptor, which do not have the extracellular domain recognised by Trastuzumab. Scaltriti proposes a method of immunofluorescence to detect the p95HER2 fragment (product of proteolysis by alpha-secretases). This new detection method can be carried out on sections of tissue embedded in paraffin and fixed with formalin following clinical protocols. The new methodology arises from observing that the truncated form p95HER2, and not the entire form of the receptor, is located in both the plasma membrane and the cytoplasm of the cell. This method proposes comparing whether there is expression of p95HER2 by means of staining the detected cytoplasm with an anti-HER2 antibody that binds the receptor's cytoplasmic domain; and confirming these results with those of a detection with an anti-cytokeratin antibody, a protein whose distribution has been extensively used as a tool for the diagnosis of tumours. However, it is not clear whether this method efficiently distinguishes those tumours expressing the complete form of HER2 from those that express the truncated forms.

The document of Pedersen et al., "A naturally occurring HER2 carboxy-terminal fragment promotes mammary tumor growth and metstasis", *Molecular and Cellular Biology*, 2009, Vol. 12, pp. 3319-3331, describes the functional relevance of the CTF-611 truncated variant of the HER2 receptor. It is shown that the presence of CTF-611 leads to the increased expression of many genes that are causally involved in metastasis, such as MMP1, ANGPTL4, MET, and IL11, and of genes that contribute to various aspects of malignant development, such as CD44, BCL2A1, ADAM9, PLAUR, and EPHA1. In vivo, expression of CTF-611 in the mouse mammary gland led to the development of aggressive tumors, which in addition led to lung metastasis at high frequency.

There is a need to locate new and efficient targets for diagnosis and therapy, properly correlated to the type of cancer in question and that make it possible to treat on time with efficient therapies those tumours having the worst prognosis, discarding from the outset those therapies that have been seen not to be effective. In view of previous studies it is necessary to distinguish the CTF-611 truncated variant of the HER2 receptor from the full-length and other truncated versions, such as p95-HER2, as CTF-611 is involved in the development of more aggressive tumors with higher tendency to metastasize compared to the other HER2 receptor forms.

The present invention offers benefits related to the problems cited above and represents a novel solution in the early classification of cancer, specifically breast cancer.

SUMMARY OF THE INVENTION

It has been determined that the presence of one of the truncated forms (CTF) of HER2, generated by the alternative initiation of translation, correlates very well with the prediction of the type of cancer to be treated, making easier the task of the physician at the moment of prescribing a course of treatment. This HER2 truncated form (CTF-611) has been identified and found to have the sequence represented by SEQ ID NO:1.

This sequence has been used to develop several tools for detecting its presence in tissue samples and preferably for distinguishing it from p95-HER2 and full-length HER2, thus providing a new and solid diagnosis set that is also applicable in clinical routine.

The present invention provides new antibodies, or fragments thereof, that recognise this truncated form CTF-611 of HER2, which is not recognised by trastuzumab. These antibodies recognize an epitope being defined by a sequence included in SEQ ID NO:2. The invention also provides hybridoma cell lines suitable for producing such antibodies. Anti-HER2 antibodies currently available recognize CTFs and HER2 or only HER2, making it very difficult to discriminate patients expressing only HER2 from patients expressing HER2 and CTFs. In contrast to available anti-HER2 antibodies, the antibodies described here preferentially bind to CTF-611, allowing the identification of patients expressing this CTF.

The antibodies provided by the present invention specifically detect CTF-611, represented by SEQ ID NO:1, and are capable of distinguishing CTF-611 from CTF-616 and preferably capable of distinguishing CTF-611 from CTF-613. The antibodies provided by the present invention, however, preferably do not bind full-length HER2 and p95-HER2.

The present invention also refers to a method of cancer diagnosis in patient samples which comprises the detection of the presence in said sample of the HER2 receptor truncated form consisting of SEQ ID NO: 1.

The present invention also provides the use of the antibody or fragment thereof of the present invention for the diagnosis and determination of prognosis in isolated samples of cancers where the HER2 receptor is expressed.

The present invention further provides an agent of diagnosis and determination of prognosis in isolated samples of cancers where the HER2 receptor and/or C-terminal fragments is expressed, which comprises at least one antibody or a fragment thereof as described above.

The present invention also provides a kit of diagnosis and determination of prognosis in isolated samples of cancers, where the HER2 receptor is expressed, that comprises means for detecting the presence in said sample of the HER2 receptor truncated form consisting of the SEQ ID NO: 1.

The invention also provides an antibody or a fragment thereof as described above for use in therapy or in the manufacture of a medicament. In particular, the medicament is for the treatment or prevention of cancers where at least the HER2 receptor truncated form consisting of the SEQ ID NO: 1 is expressed.

According to another feature of the invention, the use of antibodies or fragments is for the manufacture of a medicament for treating or preventing breast cancers in mammals, including human beings.

Another object of the present invention is a pharmaceutical composition for the treatment of cancers wherein at least the HER2 receptor truncated form consisting of SEQ ID NO: 1 is expressed, which comprises an antibody or a fragment thereof as described above and at least one pharmaceutically acceptable excipient and/or vehicle.

BRIEF DESCRIPTION OF THE DRAWINGS

(FIG. 3B). On the Y axis, N and V mean Number of Tumours and Volume of Tumours, respectively. On the X axis, T refers to Time in weeks.

DETAILED DESCRIPTION

CTF-611

As previously mentioned, the inventors found that, surprisingly, the differential detection of said HER2 truncated form with SEQ ID NO: 1 correlates very well with the manifestation of a common type of cancer in breast tissue with a poor prognosis. Thus, FIG. 3 shows the results of the evaluation of the number of tumours developed in transgenic mice expressing the truncated form CTF-611 (SEQ ID NO: 1).

Figure 3:
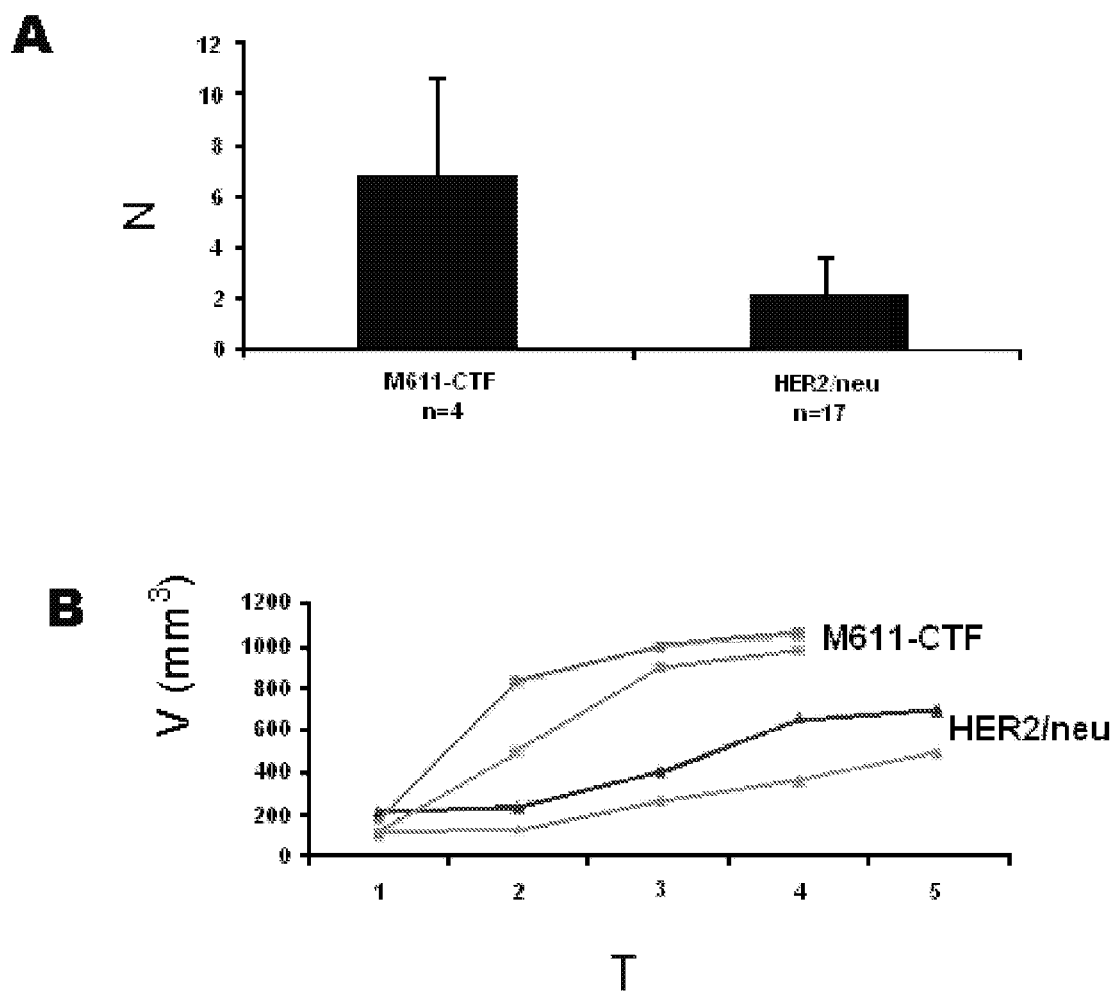
FIG. 3: Results of the evaluation of the number of tumours developed in transgenic mice that express the truncated CTF-611 (FIG. 3A) form in comparison with transgenic mice that express the complete HER2 receptor; and the results of the volume of detected tumours.

In order to obtain the results of this FIG. 3, cDNA constructs were expressed in the breast epithelium of mice, said constructs coding the human SEQ ID NO: 1 (CTF-611), identified in the figure as M611-CTF. This construct comprises the SEQ ID NO: 1 under control of the promoter of the mouse mammary tumour virus (MMTV). As control the mouse line FVB/N-Tg(MMTVneu)202J that expresses the complete form of HER2 was used, also under control of the MMTV promoter. As can be deduced from FIG. 3A, the number of tumours in mice expressing the cDNA construct with the CTF-611 form (SEQ ID NO: 1) is much higher than the one of the FVB/N-Tg(MMTVneu)202J line, identified in this figure with the designation HER2/neu. The tumours in the transgenic animals were detected at 17 weeks of age of the transgenic animals expressing CTF-611, which represents three months before the first detection in FVB/N-Tg(MMTVneu)202J mice. This fact would explain the greater aggressiveness of tumours that express HER2 fragments in relation to those tumours that express the complete form. FIG. 3B also shows that the volume of the tumours is much greater in the animals expressing the CTF truncated form of HER2 with SEQ ID NO: 1, in relation to those animals expressing constitutively the whole receptor, also known as HER2/neu. This second fact also explains the greater aggressiveness of this type of tumours. The inventors also determined that those tumours expressing the truncated form of sequence SEQ ID NO: 1 showed higher lung metastasis indices than those observed in the tumours expressing HER2/neu. Further experiments proving the clinical relevance are provided in Example 7 below.

All of this data with transgenic animals reveals that the differential detection of the HER2 receptor truncated form of SEQ ID NO: 1 in respect of the complete form of the receptor is very necessary.

Evidently, said SEQ ID NO: 1 includes all variants derived from allelic variations between individuals, which entail variations in number and type, of some amino acids, such as more or less than two or three amino acids, or the replacement of an amino acid by another one which does not modify the overall receptor's structure.

These truncated forms of HER2 can contain neo-epitopes, in other words, new antigenic determinants not present in the molecule of the whole receptor, meaning that they do not interact in the same way with the molecules as with the whole receptor (antibodies, medicaments, etc.).

Antibodies to CTF-611

The inventors could produce monoclonal antibodies to CTF-611. These antibodies recognize an epitope that is defined by a sequence included in SEQ. ID NO: 2, preferably by a sequence included in or defined by SEQ. ID NO: 3. Most preferred are antibodies that recognize an epitope that is included in or defined by MPIWKFPDEEGAS (SEQ. ID NO: 5).

In the context of the present invention, epitope is understood to mean the part of a peptidic type macromolecule (or of an antigen), whose sequence and/or spatial configuration is recognised by the immune system (antibodies, T cells, B cells).

The antibodies according to the present invention are capable of recognizing CTF-611 and distinguishing CTF-611 from CTF-616 (SEQ ID NO:7), and preferably distinguishing CTF-611 from CTF-613 (SEQ ID NO:6).

The antibodies of the present invention can preferably distinguish the protein of SEQ ID NO:1 from the HER2 receptor. Furthermore, the antibodies of the present invention can preferably distinguish the protein of SEQ ID NO:1 from the HER2 receptor truncated form 648-CTF/p95. This distinction can be visualized by one or more of immunofluorescence, flow cytometry, immunohistochemistry in cultured cells, and immunohistochemistry in samples from patients. It is particularly preferred that the distinction can be quantified both in flow cytometry and immunoprecipitation.

The antibody can be polyclonal or monoclonal.

In the sense of the present invention, "polyclonal antibody" shall be understood to mean the group of antibodies produced by different B cell lines (B lymphocytes). Polyclonal antibodies are mixtures of immunoglobulins secreted against an antigen (macromolecule), each one of these immunoglobulins being capable of recognising a different epitope, since it comes from a different B cell. Thus, within the different populations of immunoglobulins contained in a polyclonal antibody, there is a type of immunoglobulin that recognises the epitope or epitopes of interest of a specific antigen.

Polyclonal antibodies can be produced for example by conjugating the peptide of SEQ ID NO. 2, SEQ ID NO. 3, SEQ ID NO: 4 or SEQ ID NO: 5 with an immunogen such as Keyhole-limpet hemocyanin and immunizing rabbits with this conjugate.

Monoclonal antibodies can be produced using the same or similar immunogens. Hybridoma cell lines can be produced in a manner known to the skilled person. The hybridoma cell line can then be grown in a suitable culture medium from which the monoclonal antibody is recovered.

In a preferred embodiment, they are produced by the hybridoma cell lines deposited on Oct. 8, 2009 with the "Deutsche Sammlung von Mikroorganismen und Zellkulturen GmbH-DSMZ" located at Inhoffenstr. 7B, D-38124 Braunschweig, Germany, under accession numbers DSM ACC3016 (214D8c12h4) and DSM ACC3017 (226H4e8d10) in accordance with the provisions of the Treaty of Budapest.

Monoclonal antibodies produced by these hybridoma cell lines, as well as monoclonal antibodies that are functionally at least equivalent, are particularly preferred. Functionally at least equivalent are those antibodies that can discriminate between CTF-611 and CTF-616, preferably CTF-613, and between CTF-611 and HER2 equally well or even better.

Useful antibodies also include humanized and human antibodies.

Instead of the complete antibody, a fragment thereof may be used according to the present invention. The antibody fragments are selected from the group comprised by F(ab), F(ab') and Fv. In the context of the present invention, a fragment of an antibody refers to a part of the antibody which is of enough size and appropriate structure to bind to an epitope present in the HER2 receptor truncated form and thus permit its detection in a sample.

Example 3 shows specific monoclonal antibodies. Evidently, the invention extends to other polyclonal or monoclonal antibodies directed against the epitope of the CTF-611 truncated form which is defined by the sequences SEQ ID NO: 2 and SEQ ID NO: 3 that can discriminate between CTF-611 and CTF-616, preferably CTF-613, since, on the basis of the teachings of this invention they can be directly derived for a skilled in the art. Equally, the invention extends to fragments of said antibodies, such as F(ab), F(ab'), Fv, etc., or any hybridoma cell line capable of producing monoclonal antibodies directed against the peptides of SEQ ID NO:2 and SEQ ID NO: 3 that can discriminate between CTF-611 and CTF-616, preferably CTF-613.

Diagnostic Methods

In the method of diagnosis according to the invention the detection of the presence of the HER2 receptor truncated form may be carried out through means independently selected from the group comprising: detection by differential migration in a mobile phase—stationary phase system of the HER2 receptor truncated form consisting of SEQ ID NO: 1 in respect of the complete form of said HER2 receptor; and detection by binding with specific antibodies of the HER2 receptor truncated form containing the SEQ ID NO: 1.

Detection through differential migration should be understood to mean, in the context of the present invention, any analytical technique that allows separation of the compounds to be detected on the basis of their different mobility in a specific mobile phase—stationary phase system, such as an electrophoresis. Such different mobility may be caused by a different electrical charge in the compound, different molecular weight, or different affinity for other compounds.

This differential detection can be carried out through analytical techniques known by the skilled in the art such as protein electrophoresis, molecular exclusion chromatographies, antibody affinity tests, immunofluorescence, immunocytochemistry, immunohistochemistry, flow cytometry, etc. Particularly preferred is immunohistochemistry. One or more of these methods can be combined to enhance reliability.

Figure 1:
FIG. 1: Diagram of the protein sequence of the truncated form CTF-611, compared with the sequence of the complete HER2 receptor and with the truncated form known as p95 (648-CTF/p95), product of the proteolysis by alpha-secretases. The transmembrane domain is represented as a helicoidal line. The remaining molecule is indicated with a grey box. The sequence of the peptide used to generate mono and polyclonal antibodies appears underlined. The positions of intramolecular disulphide bridges are also indicated with connections between the cysteines.

Differential detection of the HER2 receptor truncated form consisting of SEQ ID NO: 1, also referred to in this invention as CTF-611, in respect of the whole or complete HER2 receptor, implies being able to visualize two proteins with different molecular weights and different sequences as can be desired from FIG. 1. The truncated form with SEQ ID NO: 1 consists of the protein resulting from the alternative initiation of translation through methionine 611 of the complete sequence of the HER2 receptor. This form or CTF thus comprises a new extracellular domain, a transmembrane fragment, and a cytosolic domain. The transmembrane fragment and the cytosolic domain are the same as those of the complete form of the HER2 receptor. Another truncated form corresponds to the one of FIG. 1 referred to as p95 or CTF-648. This last form is the product of the action of the alpha-secretases on the complete HER2 receptor, which divide a large part of the extracellular domain.

According to another embodiment of the invention, the step of detecting the presence in the sample of the HER2 receptor truncated form consisting of SEQ ID NO: 1, comprises the detection with at least one antibody as defined above. In a particular embodiment, the method of diagnosis according to the invention comprises the detection of the epitope defined by SEQ ID NO: 3.

In one embodiment of the invention, the antibodies or fragments thereof of the present invention are used as agents for the diagnosis and determination of prognosis, either directly marked in their own peptide sequence (for example with radioisotopes) or indirectly (for example by addition or binding a fluorescent agent or an agent capable of producing fluorescence by reaction in a selected reaction medium), all of the above with the aim of generating a visible signal, and if possible quantifiable, with which to detect the presence of the HER2 receptor truncated form consisting of the sequence SEQ ID NO: 1 in a sample.

In the same way, it is contemplated for the diagnosis agent containing at least the antibodies to be adhered to a solid support, directly or indirectly by means of a spacer arm. An agent of this type allows capturing of the form of sequence SEQ ID NO: 1 of a sample, in order to determine its presence afterwards with other non-specific antibodies (such as CB11).

The agents of diagnosis and determination of prognosis according to the invention can also be applied in immunohistochemistry protocols. To this effect, the (primary or secondary) monoclonal or polyclonal antibodies must be duly marked to give a visible signal, and in the best of cases quantifiable, once they have come into contact with the tested tissue and they have been allowed to interact with the proteins intended for detection, in other words, with the CTF fragment of HER2 of sequence SEQ ID NO: 1.

With the aim of facilitating the task of analysis, diagnosis and determination of the prognosis to the physician, it is contemplated that the diagnostic agent is provided in the form of a kit which includes, besides the antibodies, the reagents (e.g. reagents required for the immunohistochemical staining), buffers and detection solutions adapted to determine the presence of the truncated form of SEQ ID NO: 1 in a sample, possibly control slides representing different expression levels of CTF-611 and possibly also detailed instructions, assisting the physician in the assessment of the diagnosis. This kit may also comprise a means for carrying out a semi-quantitative immunohistochemical assay for the determination of HER2 (such as Herceptest™).

Thus, the invention provides a kit for diagnosis and determination of the prognosis, which comprises at least one antibody or a fragment thereof, said antibody or fragment being capable of recognising the epitope defined by SEQ ID NO:2 or SEQ ID NO: 3 or SEQ ID NO:5, but not capable of recognizing SEQ ID NO:6, preferably not of recognizing SEQ ID NO:7, in addition to the reagent means and buffers suitable for carrying out the interaction of the antibody with the epitope and that are extensively known by those skilled in the art.

The diagnostic method of the present invention, and the kit of the present invention, may allow the prediction of nodal metastasis, poor prognosis, and resistance to Herceptin™.

Another type of kit also object of the invention, comprises all the necessary means for carrying out detection through differential migration of the HER2 receptor truncated form consisting of the sequence SEQ ID NO: 1, in relation to the complete form of the HER2 receptor.

Within the group of cancers that express the HER2 receptor or its truncated variants, breast cancer stands out. Other cancers where these proteins are also expressed include the cancer of lung, pancreas, colon, stomach, prostate, head and neck, skin, kidney, testicle, thyroids, urinary bladder, uterus, vulva, endometrial, ovary, esophagus, mouth, salivary gland, larynx, peritoneum, nose and throat region, Fallopian tubes, Wilms tumors as well as lymphomas, Swing sarcomas, synovial sarcoma, medulloblastomas, trophoblastic tumors, glyomas, glioblastomas, cholangiocarcinomas, cholesteatoma, chondrosarcoma, ependymoma, neurilemmomas, neuromas, rhabdomyosarcomas. The diagnostic method of the present invention is thus particularly suitable for diagnosing one of these cancers. In addition to ex-vivo detection of-CTFs the antibodies could be used for in vivo imaging.

Therapeutic Methods

The antibodies of the present invention, or fragments thereof, are also useful in therapy, particularly in the therapy of cancer, particularly those cancers that express the HER2 receptor or its truncated variants. Humanized and human antibodies, and fragments thereof, are preferred.

The antibodies of this invention are used also in pharmaceutical compositions useful for the treatment of cancers in which at least the HER2 receptor truncated form consisting of SEQ ID NO: 1 is expressed. The composition comprises those pharmaceutically acceptable vehicles or excipients and at least one antibody that recognises the epitope defined by the sequences SEQ ID NO: 2 or SEQ ID NO: 3, but does not recognize SEQ ID NO:6, preferably not SEQ ID NO:7. The pharmaceutical composition may also comprise a mixture of antibodies that, besides an antibody of the present invention, contains other antibodies against HER2 or fragments thereof, such as Herceptin™.

Based on the figures provided herein and always by way of illustrative but not limiting examples, below there are described the method of diagnosis and determination of prognosis of cancers where the HER2 receptor and/or its carboxy terminals fragments (truncated variants) are expressed; new peptides and specific antibodies against said peptides; new cell lines; diagnosis agents and kits for detection, all of which being objects of the invention.

Although not specified, all technical and scientific terms used in the specification have the meaning that a skilled in the art would assign to them. Similar or equivalent methods and materials to those described herein may be used in the practice of the present invention. Throughout the description and claims the word "comprise" and variations of the word, such as "comprising", is not intended to exclude other technical features, additives, components, or steps. Additional objects, advantages and features of the invention will become apparent to those skilled in the art upon examination of the description or may be learned by practice of the invention. The following examples and drawings are provided by way of illustration, and are not intended to be limiting of the present invention.

Also, it shall be understood that the present invention covers all possible combinations of preferred and particular groups described above.

EXAMPLES

The following examples show different ways of detecting the presence of the truncated form of sequence SEQ ID NO: 1, in an isolated sample of cancer of the type that expresses the HER2 receptor and/or its truncated variants.

Experimental Procedures

Cells. MCF7 Tet-Off cells (BD bioscience) were maintained at 37° C. and 5% $CO_2$ in DMEM/F-12 (1:1)(Gibco) containing 10% FBS (Gibco), 4 mM L-Glutamine (PAA Laboratories), 0.2 mg/ml G418 (Gibco) and 1 µg/l doxycycline (Sigma). Cells were transfected with the various expression plasmids by using FuGENE6 (Roche). Single stable clones with pUHD10-3h based plasmids integrated were selected with 0.1 mg/ml hygromycin B (Invitrogen). Expression from pUHD10-3h encoded cDNAs of HER2 and CTFs was induced by removing doxycycline. First the cells were detached with 0.5% Trypsin-EDTA (GIBCO), washed three time by centrifugation and the medium changed 10 hours after seeding in culture dishes. Homogeneity of the individual clones was checked by immunofluorescence confocal microscopy with an antibody against the cytoplasmic domain of HER2. Two independently selected stable clones were used in the experiments.

Western blot. Cells expressing the different HER2 isoforms were lysed in modified RIPA buffer (20 mM $NaH_2PO_4$/NaOH pH7.4, 150 mM NaCl, 1% Triton X-100, 5 mM EDTA, 100 mM PMSF, 25 mM NaF, 16 µg/ml Aprotinin, 10 µg/ml Leupeptin and 1.3 mM $Na_3VO_4$) and protein concentrations determined with DC protein assay reagents (BIO-RAD). Samples were mixed with loading buffer (final concentrations: 62 mM Tris pH6.8, 12% glycerol, 2.5% SDS) with 5% betaMercaptoethanol and incubated at 99° C. for 5 min before fractionation of 15µg protein by SDS-PAGE. Specific signals in Western blots were quantified with the software ImageJ 1.38 (NIH).

Immunoprecipitation. Cell lysates were incubated with different antibodies for 1 hour at 4° C. Then, immunocomplexes were purified with protein A. Immunoprecipitates were washed three times with lysis buffer, mixed with loading buffer and analyzed by Western blot.

Cells for immunofluorescence microscopy seeded on glass cover-slips were washed with PBS, fixed with 4% paraformaldehyde for 20 min and permeabilized with 0.2% Triton X-100 for 10 min. For blocking and antibody binding we used PBS with 1% BSA, 0.1% Saponin and 0.02% NaN3, and for mounting Vectashield with DAPI (Vector laboratories). Antibodies were used at 1 µg/ml.

Immunohistochemistry. MCF7 cells expressing HER2, 611-CTF or 648-CTF were washed at 4° C. with PBS and detached in PBS containing 5 mM of EDTA. Then, cells were centrifuged and cell pellets were fixed in 10% neutral formalin, dehydrated and embedded in paraffin. Sections from cell pellets or from human tissues of a thickness of 4 µm were placed on poly-lysine-coated glass slides. Immunohistochemistry analyses were performed using the following protocol:
1. Deparaffinizing and Rehydrating the Section
1.1 Incubate the slides 30 min at 60° C.
1.2 Deparaffinize the slides with three 5 min. incubations of clean xylene, followed by two 3 min washes with absolute ethanol.
1.3 Gradually bring to distilled water: Ethanol 95° C. 3 min, Ethanol 70° C. 3 min, Ethanol 50° C. 3 min, distilled water.
2. Antigen Retrieval
PT Link at low pH (6), ENVISION FLEX TARGET RETRIEVAL SOLUTION HIGH pH 10×. DM 812. 20 min a 95° C.
Wash with Envision Flex wash buffer ×10 DM 811 15 min.
3. Immunohistochemical Staining
AUTOSTAINER plus Link DAKO
KIT: ENVISION FLEX+MOUSE, High pH (Link):
Envision Flex Peroxidase Blocking SM801.
Envision Flex/HRP SM 802.
Envision Flex DAB+CHROMOGEN DM 807.
Envision Flex Substrate Buffer SM 803.
Envision Flex Wash Buffer 10×DM 811.
Envision Flex Target Retrieval Solution High Ph 10×DM 812.
Envision Flex+ Mouse (linker) SM 84.
Peroxidase 5 min and wash with washing buffer.
Protein Block 5% 15-20 min.
Wash with washing buffer.
   214D8c12h4 or 226H4e8d10 at 0.2 µg/ml 2 hours.
   Wash with washing buffer.
   Secondary (Flex HRP, Flex+Mouse/Rabbit) 20 min.
   Wash with washing buffer.
   DAB 5 min.
   Wash with wash buffer.
   Hematoxylin.
   Wash with distilled water.
3. Dehydrating and Stabilizing with Mounting Medium
3.1 Gradually wash with increasing concentrations of ethanol (50%, 70%, 95%, 2 min each wash).
3.2 Gradually bring to distilled water (ethanol 95%, 70%, 50%, distilled water, 3 min each wash).
3.3 Wash with Xylene/eucalyptol (3 washes 2 min each).
3.4 Mount with DPX.
Transgenic Mice TG 611 and TG 687 mice were engineered by cloning the sequences encoding 687-CTF and 611-CTF into the multiple cloning site II downstream of the Rous sarcoma virus enhanced mouse mammary tumor virus long terminal repeat of the pMB vector (a kind gift from Dr. Marcos Malumbres, CNIO, Madrid). Founder lines were generated by microinjecting linearized plasmid DNA into fertilized oozytes harvested from superovulated FVB mice in the Centre of Animal Biotechnology and Gene Therapy (Centre de Biotecnologia Animal i Teràpia Gènica, Universitat Autònoma de Barcelona). Founder mice were genotyped by Southern hybridization analysis. After identification of founder animals, routine colony maintenance was performed by PCR genotyping. The male and female FVB/N-Tg(MMTVneu)202J mice were obtained from the Jackson Laboratory (Bar Harbor, Me.).
Whole Mounts and Histology Mammary glands were mounted on glass slides, fixed overnight in 4% paraformaldehyde and transferred to 70% ethanol. The slides were rinsed in water for 5 min and stained in a filtered solution of 0.2% carmine for 24 hours. Glands were then dehydrated sequentially with decreasing concentrations of ethanol, then defatted and stored in methyl salicylate. For histological analysis, fixed glands were blocked in paraffin, sectioned, and stained with hematoxylin and eosin.

Example 1

Detection of the Fragment of SEQ ID NO: 1 Through Differential Migration

Figure 2:
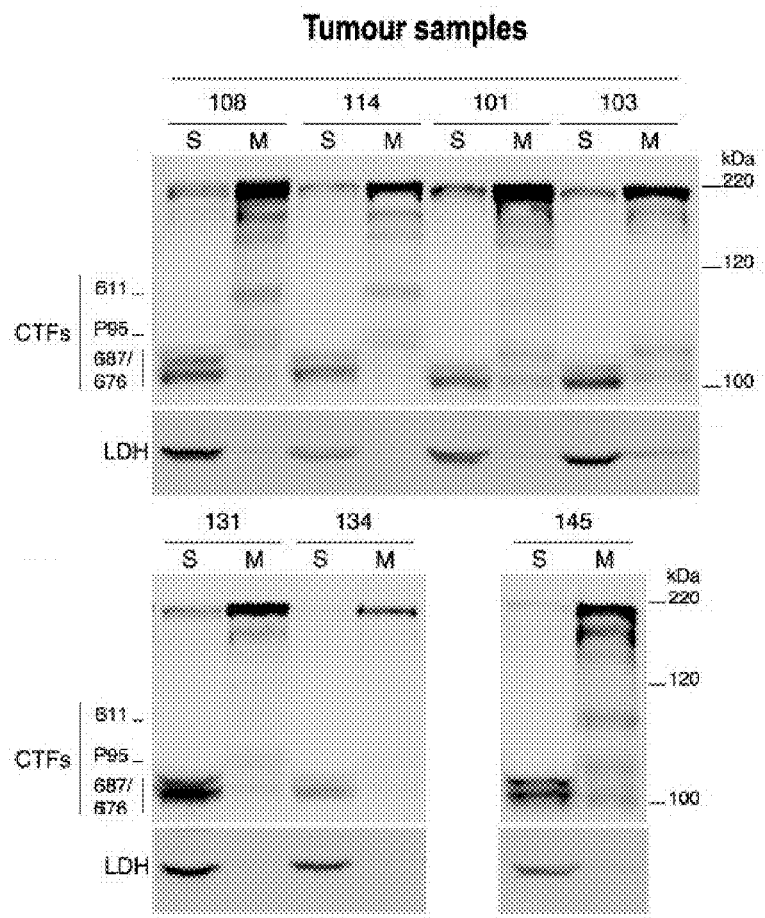
FIG. 2: Electrophoresis and Western-blot (transfer to membrane) of breast cancer samples. (S) means soluble fraction and (M) membrane fraction. In order to detect complete HER2 and the CTF-611 form, antibodies directed to the cytoplasmic domain of the proteins were used. DHL: Lacatate dehydrogenase (used as control).

In FIG. 2, which corresponds to an image of an electrophoresis gel and subsequent Western-type transfer (Western-blot), different samples of breast cancer (108, 114, 101, 103, 131, 134 and 145) were loaded on the tracks. From each sample both the soluble fraction (S) and the membrane fraction (M) of the cell lysate were analysed, in order to visualize what type of HER2 molecule was present and in what fractions. In principle, it is expected that both the complete receptor and the form of the SEQ ID NO: 1 are in the cell membrane. For the detection of complete HER2 and of CTF-611 form, antibodies were used (CB11) directed to the cytoplasmic domain of the proteins, which is a common domain in both protein forms. As an analysis' control the presence of the lactate dehydrogenase (DHL) enzyme was detected. In most samples, bands corresponding to the complete HER2 receptor and in the membrane fraction, a band corresponding to form CTF-611 of SEQ ID NO: 1 appears.

FIG. 2 therefore shows that detection of the type of truncated forms of the HER2 receptor can be carried out through a protein electrophoresis analysis. Furthermore, the presence of a fragment of HER2 of sequence SEQ ID NO: 1 is indicative of a certain type of cancer, in the case of the example, breast cancer, which needs to be evaluated and treated as an individual case within the cancers that express HER2.

Example 2

Detection of the Presence of the HER2 Fragment of Sequence SEQ ID NO: 1 with Monoclonal Antibodies Directed at Neo-Epitopes Defined by SEQ ID NO: 2 or SEQ ID NO: 3.

Using the peptide having the sequence SEQ ID NO: 4, monoclonal antibodies were obtained. This peptide corresponds to the 32 amino acids of the N-terminal end of the CTF-611 form or of SEQ ID NO:1, in which most cysteines have been replaced by serines for the purpose of conjugating it with the immunogen known as Keyhole-limpet hemocyanin (KLH).

SEQ ID NO: 4 corresponds therefore to a peptide equivalent to that of SEQ ID NO: 3, although adapted in order to carry out the immunisation technique. A skilled in the art will understand that the antibodies directed against the synthesized peptide SEQ ID NO: 4 will also recognise the epitope defined by the SEQ ID NO: 3 present in the truncated form of the HER2 receptor (SEQ ID NO: 1 or CTF-611). Similarly, a skilled in the art can follow that if the synthesized peptide used for immunisation consists of SEQ ID NO: 2, which comprises all of the amino acids of the CTF-611 receptor located in the extracellular zone, the results with antibodies directed against this other peptide are equivalent and therefore useful for the same purpose.

Figure 4:
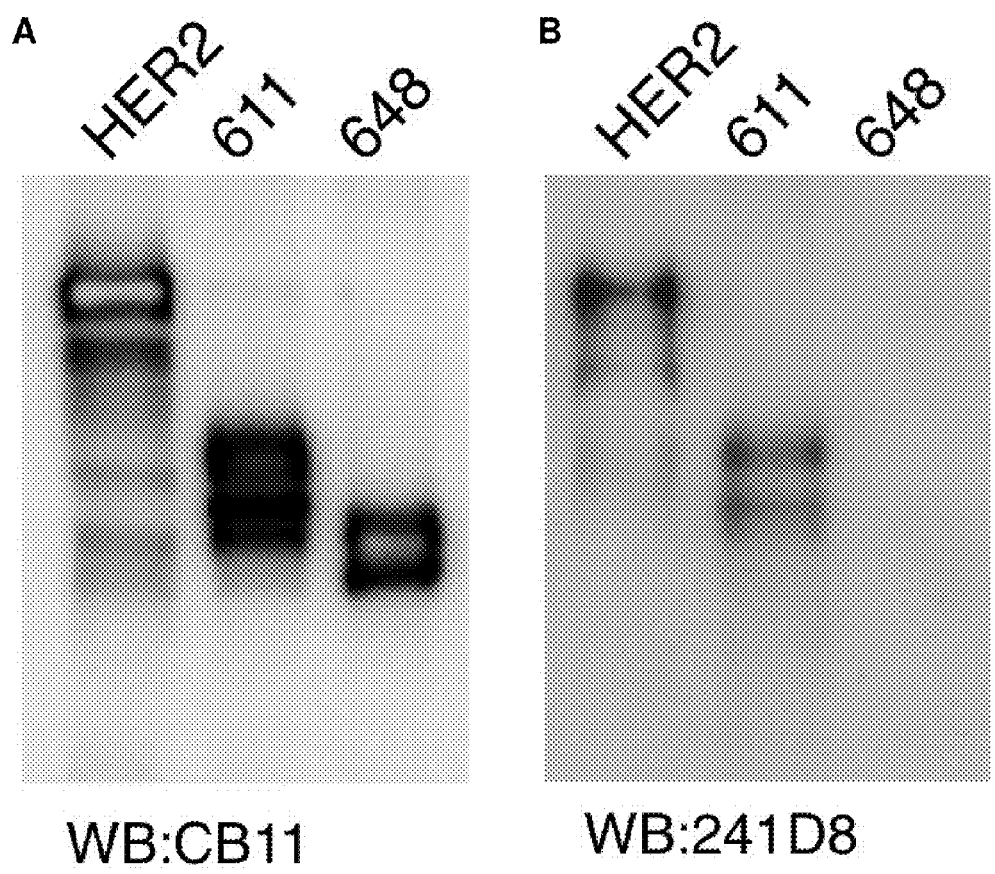
FIG. 4: Western blot: Cell lysates from MCF7 cells stably transfected with cDNA constructs encoding HER2 (left lanes), 611-CTF (middle lanes) and 648-CTF (right lanes) were analyzed with CB11 (A), a commercial monoclonal antibody directed against the intracellular domain of HER2, with the 214D8c12h4 monoclonal antibody (B), or with the 226H4e8d10 monoclonal antibody. Only the results corresponding to 214D8c12h4 are shown. Similar results were obtained with 226H4e8d10.
Figure 5:
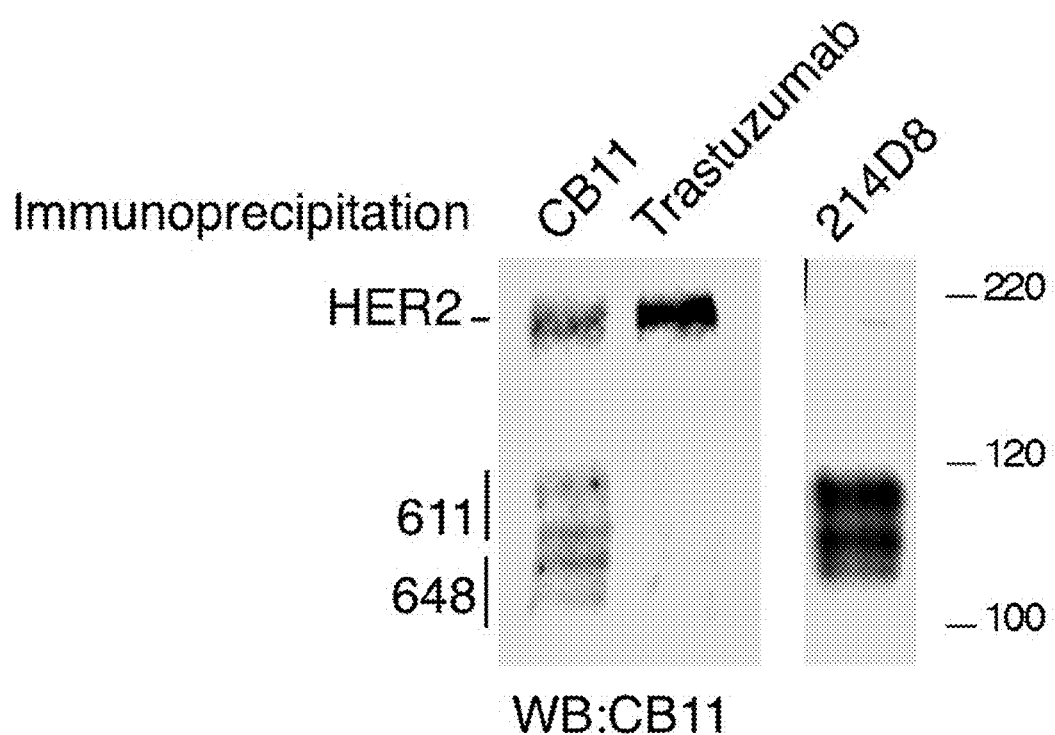
FIG. 5 Immunoprecipitation: A 1:1:1 mixture of cell lysates from MCF7 cells stably transfected with cDNA constructs encoding HER2, 611-CTF and 648-CTF was incubated with CB11, trastuzumab (a monoclonal antibody against the extracellular domain of HER2 that does not recognize 611-CTF), 214D8c12h4 or 226H4e8d10 antibodies. Immune complexes were collected with protein A, washed and analyzed by Western blot with CB11. Only the results corresponding to 214D8c12h4 are shown. Similar results were obtained with 226H4e8d10.

Monoclonal antibody 214D8c12h4 produced by the hybridoma cell line with access number DSM ACC3016 and monoclonal antibody 226H4e8d10 produced by the hybridoma cell line with access number DSM ACC3017 were selected. The results obtained with this antibody are shown in FIG. 4 and FIG. 5.

SDS-PAGE and the subsequent Western transfer with cell lysates from MCF7 cells stably transfected with cDNA constructs encoding HER2, 611-CTF and 648-CTF were carried out. These were analyzed with CB11, a commercial monoclonal antibody directed against the intracellular domain of HER2, or with the 214D8c12h4 or the 226H4e8d10 monoclonal antibody. The CB11 antibody recognizes HER2, 611-CTF and 648-CTF (FIG. 4). The monoclonal antibodies 214D8c12h4 and 226H4e8d10 recognize full-length HER2 and 611-CTF when analyzed by Western blot. Neither of the monoclonal antibodies recognizes 648-CTF, which lacks the epitope. Only the results corresponding to 214D8 are shown. Similar results were obtained with 226D8.

CTF-611 appeared in fact as two fragments of similar molecular weight. As can be derived from tests performed with Glycosidase-F, an enzyme that eliminates N-glycans from proteins (not shown), the fragment CTF-611 is a substrate of post-translational modifications. Specifically, a fragment with approximately 110 kDa corresponds to the form that is synthesized and subsequently enters into the secretary route, where it becomes N-glycosylated.

Furthermore, an immunoprecipitation assay was carried out with the monoclonal antibodies 214D8c12h4 and 226H4e8d10 in comparison with the antibody CB11 (which recognises the cytosolic domain of the receptors) and the Trastuzumab antibody (which recognizes an epitope in the extracellular domain of HER2 that is different from the epitope recognized by the antibodies according to the present invention and does not recognize CTF-611). A 1:1:1 mixture of cell lysates from MCF7 cells stably transfected with cDNA constructs encoding HER2, 611-CTF and 648-CTF was incubated with CB11, trastuzumab, 214D8c12h4 or 226H4e8d10 antibodies. Immune complexes were collected with protein A, washed and analyzed by Western blot with CB11 (FIG. 5). Only the results corresponding to 214D8c12h4 are shown. Similar results were obtained with 226H4e8d10.

While CB11 immunoprecipitates HER2 species from the three cDNA constructs, trastuzumab only immunoprecipitates full-length HER2. 214D8c12h4 and 226H4e8d10 preferentially bind to CTF-611, indicating that these antibodies are specific for this HER2 fragment and that the epitope they recognize is masked in the full-length molecule.

On the track corresponding to immunoprecipitation with the monoclonal antibody 214D8c12h4 (FIG. 5, right lane), only the bands of the glycosylated and non-glycosylated form of the CTF-611 truncated form can be distinguished. Similar results were obtained with the monoclonal antibody 226H4e8d10. Thus, the monoclonal antibodies 214D8c12h4 and 226H4e8d10 are capable of immunoprecipitating CTF-611 but not full-length HER2 and CTF-648. From this it can be concluded that the monoclonal antibodies 214D8c12h4 and 226H4e8d10 specifically recognize CTF-611 and do not show any reactivity with the full-length HER2 and CTF-648. Accordingly, they can be used for the differential and highly selective detection of what form of the HER2 receptor is expressed in an isolated sample of tumour tissue.

The characterization of monoclonal antibodies directed against a peptide corresponding to a N-terminal, 32 amino acid-long, sequence of CTF-611, confirm the existence of epitope(s) masked in full-length HER2 but exposed in CTF-611. These epitopes are masked both in the solubilized molecule and in intact cells.

Example 3

Characterization of the Epitopes Recognized by the Monoclonal Antibodies 214D8c12h4 and 226H4e8d10 Against the N-Terminus of CTF-611

Figure 6:
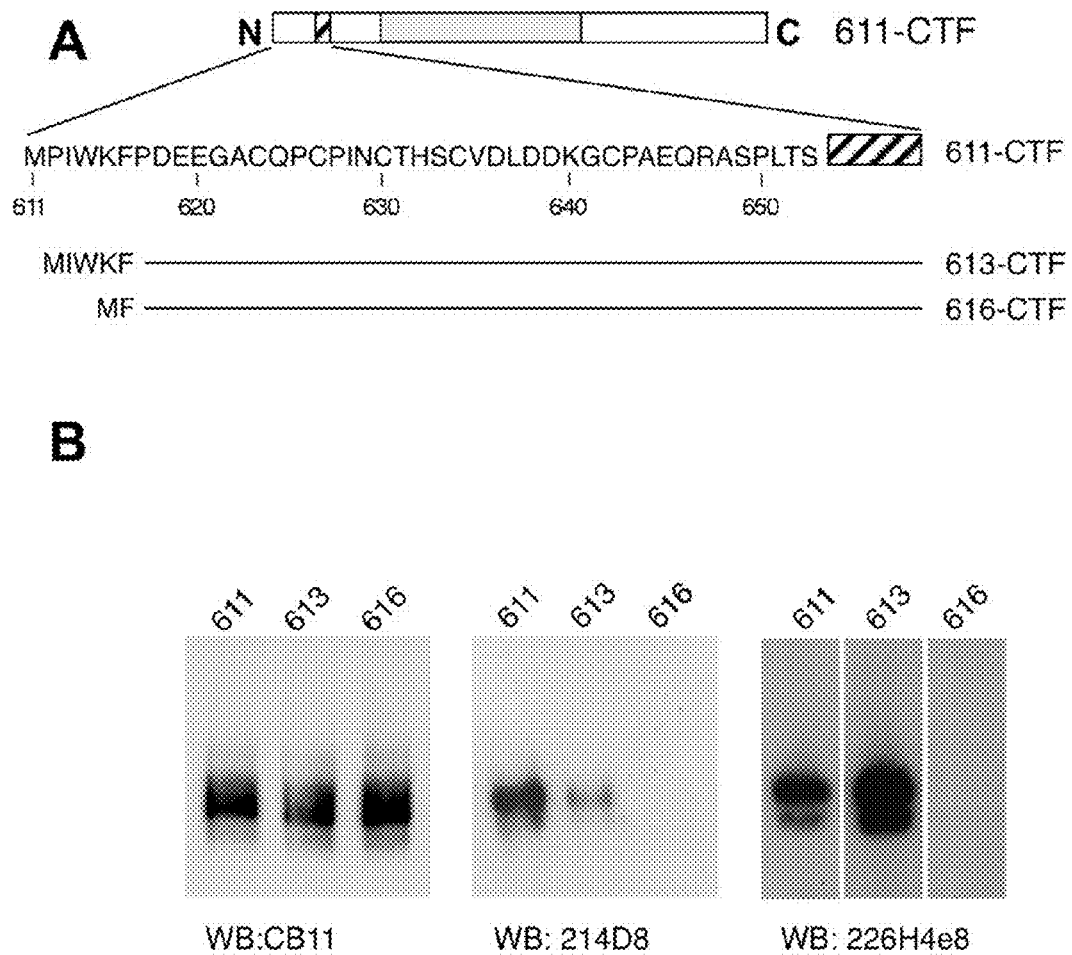
FIG. 6: Epitope mapping: A: Schematic illustrating CTF-611, CTF-613 and CTF-616 B: Western blot: Lysates from cells expressing CTF-611, CTF-613 and CTF-616 were analyzed with CB11 (left), a commercial monoclonal antibody directed against the intracellular domain of HER2, with the 214D8c12h4 monoclonal antibody (middle), or with the 226H4e8d10 monoclonal antibody (right).

FIG. 6A shows a schematic representing the primary sequence of the juxtamembrane region of CTF-611. The N- and the C-termini of the molecule are indicated. The transmembrane and the kinase domains are indicated by a dashed and a grey box, respectively. The sequence of the deletion constructs CTF-613 and CTF-616 is indicated.

In order to characterize the epitope recognized by 214D8c12h4 and 226H4e8d10 antibodies, cells transfected with cDNA constructs expressing CTF-611, CTF-613 or CTF-616 were used. Cell lysates were analyzed by Western blot with CB11 (FIG. 6B, left panel), an antibody against the cytoplasmic domain of HER2, with 214D8c12h4 (FIG. 6B, middle panel) or with 226H4e8d10 (FIG. 6B, right panel).

Conclusions. The Western blot analysis of lysates from cells expressing CTF-611, CTF-613 and CTF-616 shows that 214D8c12h4 and 226H4e8d10 antibodies recognize different epitopes. The epitope recognized by 214D8c12h4 is disrupted in the CTF-613 construct. In contrast, the epitope recognized by 226H4e8d10 is preserved in the same construct.

Example 4

Figure 7:
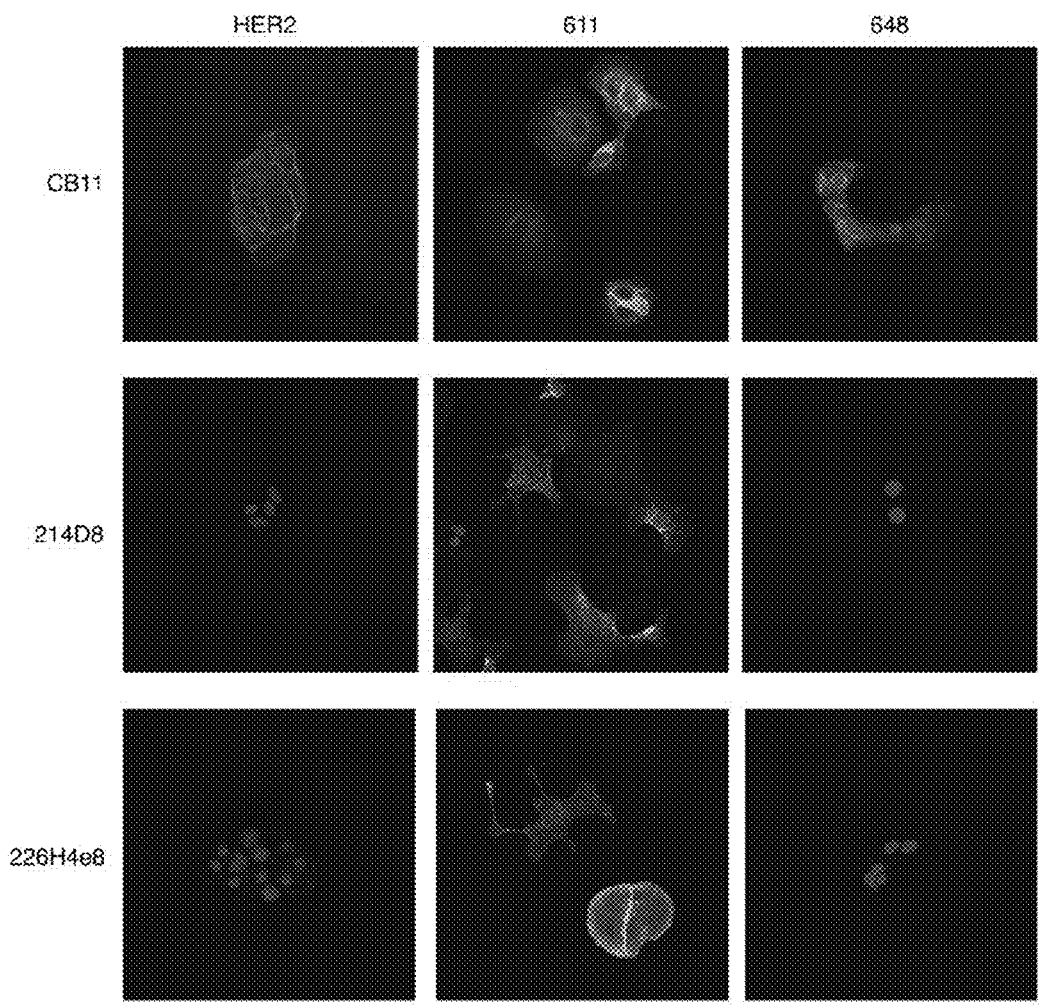
FIG. 7: Immunofluorescence: MCF7 cells stably transfected with cDNA constructs encoding HER2 (images in left column), 611-CTF (images in middle column) and 648-CTF (images in right column) were analyzed by indirect immunofluorescence with CB11, a commercial monoclonal antibody directed against the intracellular domain of HER2, with the 214D8c12h4 monoclonal antibody, or with the 226H4e8d10 monoclonal antibody.

Characterization of Monoclonal Antibodies 214D8c12h4 and 226H4e8d10 Against the N-Terminus of CTF-611 by Immunofluorescence MCF7 cells stably transfected with cDNA constructs encoding HER2, 611-CTF and 648-CTF were analyzed by indirect immunofluorescence with CB11, a commercial monoclonal antibody directed against the intracellular domain of HER2, with 214D8c12h4 monoclonal antibody or with 226H4e8d10 monoclonal antibody (FIG. 7).

As expected CB11 antibodies stain all three cell lines. The monoclonal antibodies 214D8c12h4 and 226H4e8d10 only stain CTF-611. This result shows that 214D8c12h4 and 226H4e8d10 antibodies recognize an epitope in the CTF-611 construct that is masked in the full-length molecules. Thus, these antibodies are useful tools to specifically detect the presence of CTF-611.

Example 5

Figure 8:
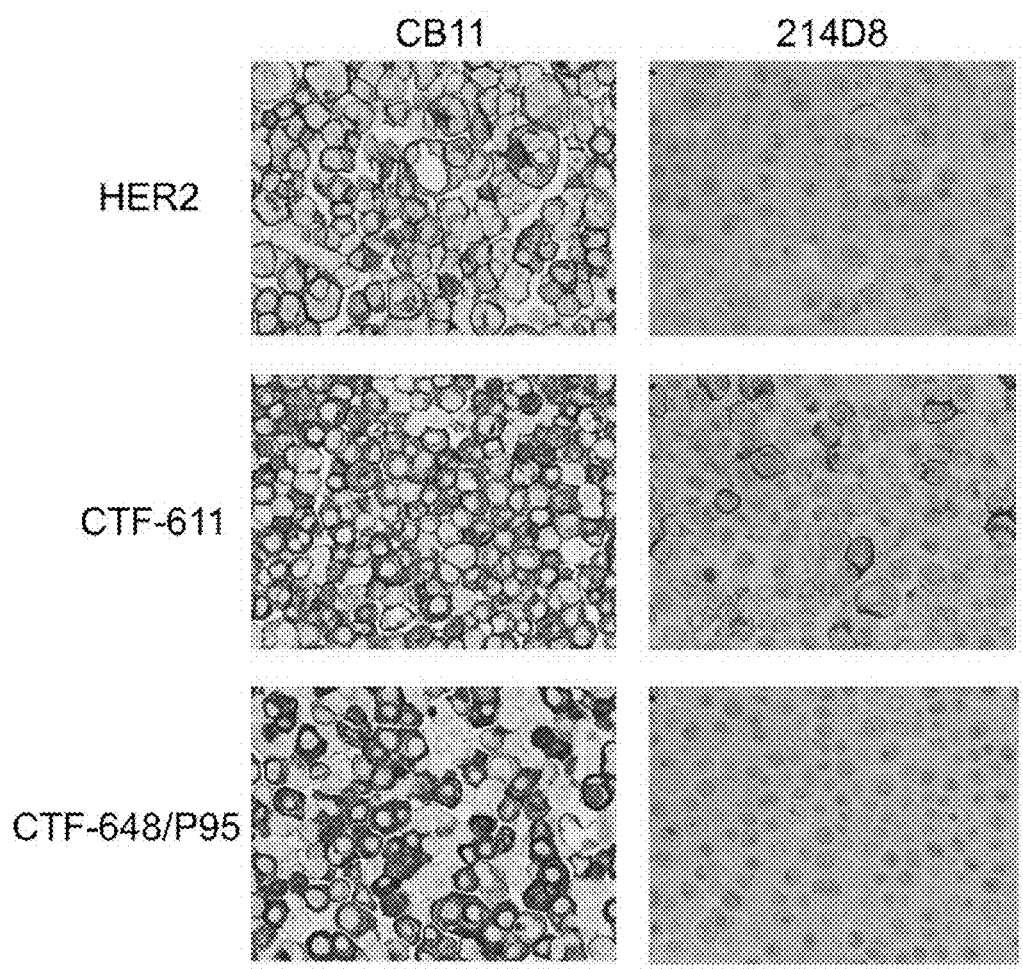
FIG. 8: Immunohistochemistry: MCF7 cells stably transfected with cDNA constructs encoding HER2, 611-CTF and 648-CTF were analyzed by immunohistochemistry with CB11 (images in left column), a commercial monoclonal antibody directed against the intracellular domain of HER2, or the 214D8c12h4 monoclonal antibody (images in right column) or the 226H4 monoclonal antibodies. Only the results corresponding to 214D8 are shown. Similar results were obtained with 226D8.

Characterization of Monoclonal Antibodies 214D8c12h4 and 226H4e8d10 Against the N-Terminus of CTF-611 by Immunohistochemistry MCF7 cells stably transfected with cDNA constructs encoding HER2, CTF-611 and 648-CTF were analyzed by immunohistochemistry with CB11, a commercial monoclonal antibody directed against the intracellular domain of HER2, with 214D8c12h4 monoclonal antibody or with 226H4e8d10 monoclonal antibody. The result is shown in FIG. 8. Only the results corresponding to 214D8c12h4 are shown. Similar results were obtained with 226H4e8d10.

Conclusions. As expected CB11 antibodies stain all three cell lines. The monoclonal antibodies 214D8c12h4 and 226H4e8d10 only stain CTF-611. This result shows that 214D8c12h4 and 226H4e8d10 antibodies recognize an epitope in the CTF-611 construct that is masked in the full-length molecules. Thus, this antibodies are useful tools to specifically detect the presence of CTF-611. This result is particularly relevant giving the fact that immunohistochemistry is the technique of choice for most routine test in the clinic.

Example 6

Generation of Animal Models to Characterize the Effect of CTF Expression In Vivo Mouse models have been instrumental in showing the oncogenic potential and relevance of HER2 in tumor progression. To characterize its oncogenic potential, we established transgenic (TG) mice expressing CTF-611 under the control of the mouse mammary tumor virus-long terminal repeat, which is preferentially active in the mammary gland. Although the cellular models indicated that soluble intracellular CTFs are inactive, to further explore the consequences of expression of these fragments, we also generated TG animals expressing 687-CTF. As a control, we used the classical and well-characterized model expressing wild type HER2 (i.e. rat neu).

At age 7 weeks, the levels of CTF-611 expressed in the heterozygous TG 611 lines F3 and F2 were ~ equal to and $\frac{1}{3}^{rd}$, respectively, the levels of endogenous HER2, while the level in F1 was below the detection threshold. The levels of 687-CTF in the homozygous lines developed varied from ~ double to half the levels of HER2 in the TG 687 lines F2 and F1, respectively.

Mammary glands of the TG animals exhibited no macroscopic abnormalities at 7 weeks age. However, morphological examination of carmine-stained whole mounts revealed hyperplastic abnormalities in the mammary ductal trees of TG HER2 mice. Similar abnormalities, albeit less pronounced, were present in all three lines of TG 611 mice. In contrast, the glands of TG 687 mice were indistinguishable from those of wild type mice.

Example 7

CTF-611 Expression Leads to the Development of Aggressive Mammary Tumors

Despite the more pronounced hyperplasia in TG HER2 mice, the three lines of TG 611 animals developed more aggressive tumors in terms of number of tumors per animal, tumor growth and tumor onset:

| Mice | Mammary Glands Average (weeks) | n |
|---|---|---|
| HER2 (Neu) | 30.3 + 7.5 | 22 |
| 611-F1 | 26.3 ± 4.6 | 6 |
| 611-F2 | 22.2 ± 4.8 | 12 |
| 611-F3 | 23.7 ± 5.5 | 3 |

(The appearance of mammary tumors was monitored by palpation weekly.)

No tumors or abnormalities were observed in TG 687 animals even after a follow-up of more than one year.

Histological analysis of the tumors showed the same typical invasive solid nodular carcinomas induced by HER2 in the TG 611 mice. The only histological difference between the tumors initiated by HER2 and CTF-611 was a higher number of mitotic images in the ones from TG 611 mice.

As previously shown, TG HER2 mice developed lung metastasis. Three to six weeks after detection of tumors, ~$\frac{1}{4}^{th}$ of the TG HER2 animals had detectable nodules in the lungs:

| Mice | Lung metastasis | n |
|---|---|---|
| HER2 (Neu) | 22 | 9 |
| 611-F1, F2, F3 | 56 | 9 |

(Mice were sacrificed 3-6 weeks after tumor detection by palpation, and the appearance of metastasis monitored by immunohistochemistry).

Histological analysis of the lung metastases confirmed the expression of HER2 and staining with cytokeratin 18 verified that the cells originated from the primary tumor. In comparison to TG HER2, the number of animals expressing CTF-611 with detectable metastases was more than double. This shows that the tumors initiated by this CTF have a more pronounced tendency to invade the lungs.

SEQUENCES

SEQ ID NO: 1

Met Pro Ile Trp Lys Phe Pro Asp Glu Glu Gly Ala
1               5                   10
Cys Gln Pro Cys Pro Ile Asn Cys Thr His Ser Cys
            15                  20
Val Asp Leu Asp Asp Lys Gly Cys Pro Ala Glu Gln
25                      30                  35
Arg Ala Ser Pro Leu Thr Ser Ile Val Ser Ala Val
                40                  45
Val Gly Ile Leu Leu Val Val Val Leu Gly Val Val
        50                  55                  60
Phe Gly Ile Leu Ile Lys Arg Arg Gln Gln Lys Ile
                    65                  70
Arg Lys Tyr Thr Met Arg Arg Leu Leu Gln Glu Thr
        75                          80
Glu Leu Val Glu Pro Leu Thr Pro Ser Gly Ala Met
85                      90                  95
Pro Asn Gln Ala Gln Met Arg Ile Leu Lys Glu Thr
                100                 105
Glu Leu Arg Lys Val Lys Val Leu Gly Ser Gly Ala
        110                 115                 120
Phe Gly Thr Val Tyr Lys Gly Ile Trp Ile Pro Asp
                    125                 130
Gly Glu Asn Val Lys Ile Pro Val Ala Ile Lys Val
                135                 140
Leu Arg Glu Asn Thr Ser Pro Lys Ala Asn Lys Glu
145                     150                 155
Ile Leu Asp Glu Ala Tyr Val Met Ala Gly Val Gly
                160                 165
Ser Pro Tyr Val Ser Arg Leu Leu Gly Ile Cys Leu
        170                 175                 180
Thr Ser Thr Val Gln Leu Val Thr Gln Leu Met Pro
                    185                 190
Tyr Gly Cys Leu Leu Asp His Val Arg Glu Asn Arg
        195                 200
Gly Arg Leu Gly Ser Gln Asp Leu Leu Asn Trp Cys
205                     210                 215
Met Gln Ile Ala Lys Gly Met Ser Tyr Leu Glu Asp
                220                 225
Val Arg Leu Val His Arg Asp Leu Ala Ala Arg Asn
230                     235                 240
Val Leu Val Lys Ser Pro Asn His Val Lys Ile Thr
                    245                 250
Asp Phe Gly Leu Ala Arg Leu Leu Asp Ile Asp Glu
                255                 260

```
Thr Glu Tyr His Ala Asp Gly Gly Lys Val Pro Ile
265                 270                 275
Lys Trp Met Ala Leu Glu Ser Ile Leu Arg Arg Arg
            280                 285
Phe Thr His Gln Ser Asp Val Trp Ser Tyr Gly Val
        290                 295                 300
Thr Val Trp Glu Leu Met Thr Phe Gly Ala Lys Pro
                    305                 310
Tyr Asp Gly Ile Pro Ala Arg Glu Ile Pro Asp Leu
            315                 320
Leu Glu Lys Gly Glu Arg Leu Pro Gln Pro Pro Ile
325                 330                 335
Cys Thr Ile Asp Val Tyr Met Ile Met Val Lys Cys
            340                 345
Trp Met Ile Asp Ser Glu Cys Arg Pro Arg Phe Arg
        350                 355                 360
Glu Leu Val Ser Glu Phe Ser Arg Met Ala Arg Asp
                365                 370
Pro Gln Arg Phe Val Val Ile Gln Asn Glu Asp Leu
            375                 380
Gly Pro Ala Ser Pro Leu Asp Ser Thr Phe Tyr Arg
385                 390                 395
Ser Leu Leu Glu Asp Asp Asp Met Gly Asp Leu Val
                400                 405
Asp Ala Glu Glu Tyr Leu Val Pro Gln Gln Gly Phe
410                 415                 420
Phe Cys Pro Asp Pro Ala Pro Gly Ala Gly Gly Met
                    425                 430
Val His His Arg His Arg Ser Ser Ser Thr Arg Ser
            435                 440
Gly Gly Gly Asp Leu Thr Leu Gly Leu Glu Pro Ser
445                 450                 455
Glu Glu Glu Ala Pro Arg Ser Pro Leu Ala Pro Ser
                460                 465
Glu Gly Ala Gly Ser Asp Val Phe Asp Gly Asp Leu
                470                 475                 480
Gly Met Gly Ala Ala Lys Gly Leu Gln Ser Leu Pro
            485                 490
Thr His Asp Pro Ser Pro Leu Gln Arg Tyr Ser Glu
        495                 500
Asp Pro Thr Val Pro Leu Pro Ser Glu Thr Asp Gly
505                 510                 515
Tyr Val Ala Pro Leu Thr Cys Ser Pro Gln Pro Glu
            520                 525
Tyr Val Asn Gln Pro Asp Val Arg Pro Gln Pro Pro
        530                 535                 540
Ser Pro Arg Glu Gly Pro Leu Pro Ala Ala Arg Pro
                545                 550
Ala Gly Ala Thr Leu Glu Arg Ala Lys Thr Leu Ser
            555                 560
Pro Gly Lys Asn Gly Val Val Lys Asp Val Phe Ala
565                 570                 575
Phe Gly Gly Ala Val Glu Asn Pro Glu Tyr Leu Thr
                580                 585
Pro Gln Gly Gly Ala Ala Pro Gln Pro His Pro Pro
        590                 595                 600
Pro Ala Phe Ser Pro Ala Phe Asp Asn Leu Tyr Tyr
                605                 610
Trp Asp Gln Asp Pro Pro Glu Arg Gly Ala Pro Pro
            615                 620
Ser Thr Phe Lys Gly Thr Pro Thr Ala Glu Asn Pro
625                 630                 635
Glu Tyr Leu Gly Leu Asp Val Pro Val
                640                 645

SEQ ID NO: 2
Met Pro Ile Trp Lys Phe Pro Asp Glu Glu Gly Ala
1                   5                   10
Cys Gln Pro Cys Pro Ile Asn Cys Thr His Ser Cys
            15                  20
Val Asp Leu Asp Asp Lys Gly Cys Pro Ala Glu Gln
25                  30                  35
Arg Ala Ser Pro Leu Thr
                40

SEQ ID NO: 3
Met Pro Ile Trp Lys Phe Pro Asp Glu Glu Gly Ala
1                   5                   10
Cys Gln Pro Cys Pro Ile Asn Cys Thr His Ser Cys
            15                  20
Val Asp Leu Asp Asp Lys Gly Cys
25                  30

SEQ ID NO: 4
Met Pro Ile Trp Lys Phe Pro Asp Glu Glu Gly Ala
1                   5                   10
Ser Gln Pro Ser Pro Ile Asn Ser Thr His Ser Ser
            15                  20
Val Asp Leu Asp Asp Lys Gly Cys
25                  30

SEQ ID NO: 5
Met Pro Ile Trp Lys Phe Pro Asp Glu Glu Gly Ala
1                   5                   10
Ser

SEQ ID NO: 6
Met Ile Trp Lys Phe Pro Asp Glu Glu Gly Ala Cys
1                   5                   10
Gln Pro Cys Pro Ile Asn Cys Thr His Ser Cys Val
            15                  20
Asp Leu Asp Asp Lys Gly Cys Pro Ala Glu Gln Arg
25                  30                  35
Ala Ser Pro Leu Thr Ser Ile Val Ser Ala Val Val
                40                  45
Gly Ile Leu Leu Val Val Val Leu Gly Val Val Phe
            50                  55                  60
Gly Ile Leu Ile Lys Arg Arg Gln Gln Lys Ile Arg
                    65                  70
Lys Tyr Thr Met Arg Arg Leu Leu Gln Glu Thr Glu
            75                  80
Leu Val Glu Pro Leu Thr Pro Ser Gly Ala Met Pro
85                  90                  95
Asn Gln Ala Gln Met Arg Ile Leu Lys Glu Thr Glu
                100                 105
Leu Arg Lys Val Lys Val Leu Gly Ser Gly Ala Phe
            110                 115                 120
Gly Thr Val Tyr Lys Gly Ile Trp Ile Pro Asp Gly
                    125                 130
Glu Asn Val Lys Ile Pro Val Ala Ile Lys Val Leu
            135                 140
Arg Glu Asn Thr Ser Pro Lys Ala Asn Lys Glu Ile
145                 150                 155
Leu Asp Glu Ala Tyr Val Met Ala Gly Val Gly Ser
                160                 165
Pro Tyr Val Ser Arg Leu Leu Gly Ile Cys Leu Thr
            170                 175                 180
Ser Thr Val Gln Leu Val Thr Gln Leu Met Pro Tyr
                    185                 190
Gly Cys Leu Leu Asp His Val Arg Glu Asn Arg Gly
            195                 200
Arg Leu Gly Ser Gln Asp Leu Leu Asn Trp Cys Met
205                 210                 215
Gln Ile Ala Lys Gly Met Ser Tyr Leu Glu Asp Val
                220                 225
Arg Leu Val His Arg Asp Leu Ala Ala Arg Asn Val
            230                 235                 240
Leu Val Lys Ser Pro Asn His Val Lys Ile Thr Asp
                    245                 250
Phe Gly Leu Ala Arg Leu Leu Asp Ile Asp Glu Thr
            255                 260
Glu Tyr His Ala Asp Gly Gly Lys Val Pro Ile Lys
265                 270                 275
Trp Met Ala Leu Glu Ser Ile Leu Arg Arg Arg Phe
                280                 285
Thr His Gln Ser Asp Val Trp Ser Tyr Gly Val Thr
            290                 295                 300
Val Trp Glu Leu Met Thr Phe Gly Ala Lys Pro Tyr
                    305                 310
Asp Gly Ile Pro Ala Arg Glu Ile Pro Asp Leu Leu
            315                 320
Glu Lys Gly Glu Arg Leu Pro Gln Pro Pro Ile Cys
325                 330                 335
Thr Ile Asp Val Tyr Met Ile Met Val Lys Cys Trp
                340                 345
Met Ile Asp Ser Glu Cys Arg Pro Arg Phe Arg Glu
            350                 355                 360
Leu Val Ser Glu Phe Ser Arg Met Ala Arg Asp Pro
                    365                 370
Gln Arg Phe Val Val Ile Gln Asn Glu Asp Leu Gly
            375                 380
```

-continued

```
Pro Ala Ser Pro Leu Asp Ser Thr Phe Tyr Arg Ser
385                 390                 395
Leu Leu Glu Asp Asp Asp Met Gly Asp Leu Val Asp
                400                 405
Ala Glu Glu Tyr Leu Val Pro Gln Gln Gly Phe Phe
410                 415                 420
Cys Pro Asp Pro Ala Pro Gly Ala Gly Gly Met Val
                425                 430
His His Arg His Arg Ser Ser Ser Thr Arg Ser Gly
            435                 440
Gly Gly Asp Leu Thr Leu Gly Leu Glu Pro Ser Glu
445                 450                 455
Glu Glu Ala Pro Arg Ser Pro Leu Ala Pro Ser Glu
                460                 465
Gly Ala Gly Ser Asp Val Phe Asp Gly Asp Leu Gly
            470                 475                 480
Met Gly Ala Ala Lys Gly Leu Gln Ser Leu Pro Thr
                485                 490
His Asp Pro Ser Pro Leu Gln Arg Tyr Ser Glu Asp
                495                 500
Pro Thr Val Pro Leu Pro Ser Glu Thr Asp Gly Tyr
505                 510                 515
Val Ala Pro Leu Thr Cys Ser Pro Gln Pro Glu Tyr
                520                 525
Val Asn Gln Pro Asp Val Arg Pro Gln Pro Pro Ser
530                 535                 540
Pro Arg Glu Gly Pro Leu Pro Ala Ala Arg Pro Ala
                545                 550
Gly Ala Thr Leu Glu Arg Ala Lys Thr Leu Ser Pro
            555                 560
Gly Lys Asn Gly Val Val Lys Asp Val Phe Ala Phe
565                 570                 575
Gly Gly Ala Val Glu Asn Pro Glu Tyr Leu Thr Pro
                580                 585
Gln Gly Gly Ala Ala Pro Gln Pro His Pro Pro Pro
590                 595                 600
Ala Phe Ser Pro Ala Phe Asp Asn Leu Tyr Tyr Trp
                605                 610
Asp Gln Asp Pro Pro Glu Arg Gly Ala Pro Pro Ser
            615                 620
Thr Phe Lys Gly Thr Pro Thr Ala Glu Asn Pro Glu
625                 630                 635
Tyr Leu Gly Leu Asp Val Pro Val
                640

SEQ ID NO: 7
Met Phe Pro Asp Glu Glu Gly Ala Cys Gln Pro Cys
1                   5                   10
Pro Ile Asn Cys Thr His Ser Cys Val Asp Leu Asp
            15                  20
Asp Lys Gly Cys Pro Ala Glu Gln Arg Ala Ser Pro
25                  30                  35
Leu Thr Ser Ile Val Ser Ala Val Val Gly Ile Leu
            40                  45
Leu Val Val Val Leu Gly Val Val Phe Gly Ile Leu
            50                  55                  60
Ile Lys Arg Arg Gln Gln Lys Ile Arg Lys Tyr Thr
                65                  70
Met Arg Arg Leu Leu Gln Glu Thr Glu Leu Val Glu
            75                  80
Pro Leu Thr Pro Ser Gly Ala Met Pro Asn Gln Ala
85                  90                  95
Gln Met Arg Ile Leu Lys Glu Thr Glu Leu Arg Lys
                100                 105
Val Lys Val Leu Gly Ser Gly Ala Phe Gly Thr Val
            110                 115                 120
Tyr Lys Gly Ile Trp Ile Pro Asp Gly Glu Asn Val
                125                 130
Lys Ile Pro Val Ala Ile Lys Val Leu Arg Glu Asn
                135                 140
Thr Ser Pro Lys Ala Asn Lys Glu Ile Leu Asp Glu
            145                 150                 155
Ala Tyr Val Met Ala Gly Val Gly Ser Pro Tyr Val
                160                 165
Ser Arg Leu Leu Gly Ile Cys Leu Thr Ser Thr Val
            170                 175                 180
Gln Leu Val Thr Gln Leu Met Pro Tyr Gly Cys Leu
                185                 190
Leu Asp His Val Arg Glu Asn Arg Gly Arg Leu Gly
                195                 200
Ser Gln Asp Leu Leu Asn Trp Cys Met Gln Ile Ala
                205                 210                 215
Lys Gly Met Ser Tyr Leu Glu Asp Val Arg Leu Val
            220                 225
His Arg Asp Leu Ala Ala Arg Asn Val Leu Val Lys
                230                 235                 240
Ser Pro Asn His Val Lys Ile Thr Asp Phe Gly Leu
                245                 250
Ala Arg Leu Leu Asp Ile Asp Glu Thr Glu Tyr His
                255                 260
Ala Asp Gly Gly Lys Val Pro Ile Lys Trp Met Ala
265                 270                 275
Leu Glu Ser Ile Leu Arg Arg Arg Phe Thr His Gln
                280                 285
Ser Asp Val Trp Ser Tyr Gly Val Thr Val Trp Glu
                290                 295                 300
Leu Met Thr Phe Gly Ala Lys Pro Tyr Asp Gly Ile
                305                 310
Pro Ala Arg Glu Ile Pro Asp Leu Leu Glu Lys Gly
                315                 320
Glu Arg Leu Pro Gln Pro Pro Ile Cys Thr Ile Asp
                325                 330                 335
Val Tyr Met Ile Met Val Lys Cys Trp Met Ile Asp
                340                 345
Ser Glu Cys Arg Pro Arg Phe Arg Glu Leu Val Ser
                350                 355                 360
Glu Phe Ser Arg Met Ala Arg Asp Pro Gln Arg Phe
                365                 370
Val Val Ile Gln Asn Glu Asp Leu Gly Pro Ala Ser
                375                 380
Pro Leu Asp Ser Thr Phe Tyr Arg Ser Leu Leu Glu
385                 390                 395
Asp Asp Asp Met Gly Asp Leu Val Asp Ala Glu Glu
                400                 405
Tyr Leu Val Pro Gln Gln Gly Phe Phe Cys Pro Asp
410                 415                 420
Pro Ala Pro Gly Ala Gly Gly Met Val His His Arg
                425                 430
His Arg Ser Ser Ser Thr Arg Ser Gly Gly Gly Asp
            435                 440
Leu Thr Leu Gly Leu Glu Pro Ser Glu Glu Glu Ala
445                 450                 455
Pro Arg Ser Pro Leu Ala Pro Ser Glu Gly Ala Gly
                460                 465
Ser Asp Val Phe Asp Gly Asp Leu Gly Met Gly Ala
            470                 475                 480
Ala Lys Gly Leu Gln Ser Leu Pro Thr His Asp Pro
                485                 490
Ser Pro Leu Gln Arg Tyr Ser Glu Asp Pro Thr Val
                495                 500
Pro Leu Pro Ser Glu Thr Asp Gly Tyr Val Ala Pro
505                 510                 515
Leu Thr Cys Ser Pro Gln Pro Glu Tyr Val Asn Gln
                520                 525
Pro Asp Val Arg Pro Gln Pro Pro Ser Pro Arg Glu
                530                 535                 540
Gly Pro Leu Pro Ala Ala Arg Pro Ala Gly Ala Thr
                545                 550
Leu Glu Arg Ala Lys Thr Leu Ser Pro Gly Lys Asn
            555                 560
Gly Val Val Lys Asp Val Phe Ala Phe Gly Gly Ala
565                 570                 575
Val Glu Asn Pro Glu Tyr Leu Thr Pro Gln Gly Gly
                580                 585
Ala Ala Pro Gln Pro His Pro Pro Pro Ala Phe Ser
                590                 595                 600
Pro Ala Phe Asp Asn Leu Tyr Tyr Trp Asp Gln Asp
                605                 610
Pro Pro Glu Arg Gly Ala Pro Pro Ser Thr Phe Lys
                615                 620
Gly Thr Pro Thr Ala Glu Asn Pro Glu Tyr Leu Gly
625                 630                 635
Leu Asp Val Pro Val
                640
```

SEQUENCE LISTING FREE TEXT

SEQ ID NO: 1 Truncated form or Carboxy Terminal Fragment (CTF) of the human protein HER2

SEQ ID NO: 2 Epitope of a truncated form of the human HER2 protein
SEQ ID NO: 3 Epitope of a truncated form of the human HER2 protein
SEQ ID NO: 4 Synthetic peptide derived from an epitope of a truncated form of the human HER2 protein
SEQ ID NO: 5 Synthetic peptide derived from an epitope of a truncated form of the human HER2 protein
SEQ ID NO: 6 Carboxy Terminal Fragment (CTF) of the human protein HER2 CTF-613
SEQ ID NO: 7 Carboxy Terminal Fragment (CTF) of the human protein HER2 CTF-616

The invention claimed is:

1. An isolated antibody or a fragment thereof that recognizes an epitope of a truncated form of HER2 receptor, wherein said antibody is produced by the hybridoma cell line deposited with the "Deutsche Sammlung von Mikroorganismen und Zellen-DSMZ" with accession number DSM ACC3016 or the hybridoma cell line deposited with the "Deutsche Sammlung von Mikroorganismen und Zellen-DSMZ" with accession number DSM ACC3017.

2. The isolated antibody or fragment according to claim 1, wherein the fragment is one selected from the group consisting of F(ab), F(ab') and Fv.

3. A hybridoma producing the antibody of claim 1.

4. A method for obtaining an antibody from the hybridoma of claim 3, comprising growing the hybridoma cell line according to claim 3 in a suitable culture medium and recovering the antibody from the medium.

5. An agent for diagnosis and determination of prognosis in isolated samples of cancers of the type that express the HER2 receptor or its truncated variants, which comprises at least one antibody or a fragment thereof according to claim 1.

6. The agent for diagnosis according to claim 5, wherein the antibody or fragment thereof is arranged on a solid support.

7. A kit for diagnosis and determination of prognosis in isolated samples of cancers of the type that express the HER2 receptor or its truncated variants, wherein the kit comprises at least one agent according to claim 5.

8. A pharmaceutical composition comprising the isolated antibody or a fragment thereof according to claim 1 in an amount effective to treat a cancer that is associated with the expression of the truncated form of HER2 receptor containing the amino acid sequence of SEQ ID NO: 1; and at least one pharmaceutically acceptable excipient and/or vehicle.

9. A method of cancer diagnosis, which comprises the detection of the presence of the truncated form of HER2 receptor consisting of the amino acid sequence SEQ ID NO: 1 in a patient sample, using one or more antibodies as defined claim 1.

10. The method according to claim 9, which is a prognostic method allowing the prognosis of progression of tumor growth and/or metastases.

* * * * *

```
                        SEQUENCE LISTING

<160> NUMBER OF SEQ ID NOS: 7

<210> SEQ ID NO 1
<211> LENGTH: 645
<212> TYPE: PRT
<213> ORGANISM: Homo sapiens

<400> SEQUENCE: 1

Met Pro Ile Trp Lys Phe Pro Asp Glu Glu Gly Ala Cys Gln Pro Cys
1               5                   10                  15

Pro Ile Asn Cys Thr His Ser Cys Val Asp Leu Asp Asp Lys Gly Cys
            20                  25                  30

Pro Ala Glu Gln Arg Ala Ser Pro Leu Thr Ser Ile Val Ser Ala Val
        35                  40                  45

Val Gly Ile Leu Leu Val Val Val Leu Gly Val Val Phe Gly Ile Leu
    50                  55                  60

Ile Lys Arg Arg Gln Gln Lys Ile Arg Lys Tyr Thr Met Arg Arg Leu
65                  70                  75                  80

Leu Gln Glu Thr Glu Leu Val Glu Pro Leu Thr Pro Ser Gly Ala Met
                85                  90                  95

Pro Asn Gln Ala Gln Met Arg Ile Leu Lys Glu Thr Glu Leu Arg Lys
            100                 105                 110

Val Lys Val Leu Gly Ser Gly Ala Phe Gly Thr Val Tyr Lys Gly Ile
        115                 120                 125

Trp Ile Pro Asp Gly Glu Asn Val Lys Ile Pro Val Ala Ile Lys Val
    130                 135                 140

Leu Arg Glu Asn Thr Ser Pro Lys Ala Asn Lys Glu Ile Leu Asp Glu
145                 150                 155                 160

Ala Tyr Val Met Ala Gly Val Gly Ser Pro Tyr Val Ser Arg Leu Leu
                165                 170                 175

Gly Ile Cys Leu Thr Ser Thr Val Gln Leu Val Thr Gln Leu Met Pro
            180                 185                 190

Tyr Gly Cys Leu Leu Asp His Val Arg Glu Asn Arg Gly Arg Leu Gly
        195                 200                 205

Ser Gln Asp Leu Leu Asn Trp Cys Met Gln Ile Ala Lys Gly Met Ser
    210                 215                 220

Tyr Leu Glu Asp Val Arg Leu Val His Arg Asp Leu Ala Ala Arg Asn
225                 230                 235                 240

Val Leu Val Lys Ser Pro Asn His Val Lys Ile Thr Asp Phe Gly Leu
                245                 250                 255

Ala Arg Leu Leu Asp Ile Asp Glu Thr Glu Tyr His Ala Asp Gly Gly
            260                 265                 270

Lys Val Pro Ile Lys Trp Met Ala Leu Glu Ser Ile Leu Arg Arg Arg
        275                 280                 285

Phe Thr His Gln Ser Asp Val Trp Ser Tyr Gly Val Thr Val Trp Glu
    290                 295                 300

Leu Met Thr Phe Gly Ala Lys Pro Tyr Asp Gly Ile Pro Ala Arg Glu
305                 310                 315                 320
```

```
Ile Pro Asp Leu Leu Glu Lys Gly Glu Arg Leu Pro Gln Pro Pro Ile
            325                 330                 335

Cys Thr Ile Asp Val Tyr Met Ile Met Val Lys Cys Trp Met Ile Asp
            340                 345                 350

Ser Glu Cys Arg Pro Arg Phe Arg Glu Leu Val Ser Glu Phe Ser Arg
            355                 360                 365

Met Ala Arg Asp Pro Gln Arg Phe Val Val Ile Gln Asn Glu Asp Leu
370                 375                 380

Gly Pro Ala Ser Pro Leu Asp Ser Thr Phe Tyr Arg Ser Leu Leu Glu
385                 390                 395                 400

Asp Asp Asp Met Gly Asp Leu Val Asp Ala Glu Glu Tyr Leu Val Pro
            405                 410                 415

Gln Gln Gly Phe Phe Cys Pro Asp Pro Ala Pro Gly Ala Gly Gly Met
            420                 425                 430

Val His His Arg His Arg Ser Ser Ser Thr Arg Ser Gly Gly Gly Asp
            435                 440                 445

Leu Thr Leu Gly Leu Glu Pro Ser Glu Glu Glu Ala Pro Arg Ser Pro
            450                 455                 460

Leu Ala Pro Ser Glu Gly Ala Gly Ser Asp Val Phe Asp Gly Asp Leu
465                 470                 475                 480

Gly Met Gly Ala Ala Lys Gly Leu Gln Ser Leu Pro Thr His Asp Pro
            485                 490                 495

Ser Pro Leu Gln Arg Tyr Ser Glu Asp Pro Thr Val Pro Leu Pro Ser
            500                 505                 510

Glu Thr Asp Gly Tyr Val Ala Pro Leu Thr Cys Ser Pro Gln Pro Glu
            515                 520                 525

Tyr Val Asn Gln Pro Asp Val Arg Pro Gln Pro Pro Ser Pro Arg Glu
            530                 535                 540

Gly Pro Leu Pro Ala Ala Arg Pro Ala Gly Ala Thr Leu Glu Arg Ala
545                 550                 555                 560

Lys Thr Leu Ser Pro Gly Lys Asn Gly Val Val Lys Asp Val Phe Ala
            565                 570                 575

Phe Gly Gly Ala Val Glu Asn Pro Glu Tyr Leu Thr Pro Gln Gly Gly
            580                 585                 590

Ala Ala Pro Gln Pro His Pro Pro Ala Phe Ser Pro Ala Phe Asp
            595                 600                 605

Asn Leu Tyr Tyr Trp Asp Gln Asp Pro Pro Glu Arg Gly Ala Pro Pro
            610                 615                 620

Ser Thr Phe Lys Gly Thr Pro Thr Ala Glu Asn Pro Glu Tyr Leu Gly
625                 630                 635                 640

Leu Asp Val Pro Val
            645

<210> SEQ ID NO 2
<211> LENGTH: 42
<212> TYPE: PRT
<213> ORGANISM: Homo sapiens

<400> SEQUENCE: 2

Met Pro Ile Trp Lys Phe Pro Asp Glu Glu Gly Ala Cys Gln Pro Cys
1               5                   10                  15

Pro Ile Asn Cys Thr His Ser Cys Val Asp Leu Asp Asp Lys Gly Cys
            20                  25                  30

Pro Ala Glu Gln Arg Ala Ser Pro Leu Thr
            35                  40
```

-continued

```
<210> SEQ ID NO 3
<211> LENGTH: 32
<212> TYPE: PRT
<213> ORGANISM: Homo sapiens

<400> SEQUENCE: 3

Met Pro Ile Trp Lys Phe Pro Asp Glu Glu Gly Ala Cys Gln Pro Cys
1               5                   10                  15

Pro Ile Asn Cys Thr His Ser Cys Val Asp Leu Asp Asp Lys Gly Cys
            20                  25                  30

<210> SEQ ID NO 4
<211> LENGTH: 32
<212> TYPE: PRT
<213> ORGANISM: Artificial
<220> FEATURE:
<223> OTHER INFORMATION: Synthetic peptide derived from an epitope of a
      truncated form of the human HER2 protein

<400> SEQUENCE: 4

Met Pro Ile Trp Lys Phe Pro Asp Glu Glu Gly Ala Ser Gln Pro Ser
1               5                   10                  15

Pro Ile Asn Ser Thr His Ser Ser Val Asp Leu Asp Asp Lys Gly Cys
            20                  25                  30

<210> SEQ ID NO 5
<211> LENGTH: 13
<212> TYPE: PRT
<213> ORGANISM: Artificial
<220> FEATURE:
<223> OTHER INFORMATION: Synthetic peptide derived from an epitope of a
      truncated form of the human HER2 protein

<400> SEQUENCE: 5

Met Pro Ile Trp Lys Phe Pro Asp Glu Glu Gly Ala Ser
1               5                   10

<210> SEQ ID NO 6
<211> LENGTH: 644
<212> TYPE: PRT
<213> ORGANISM: Homo sapiens

<400> SEQUENCE: 6

Met Ile Trp Lys Phe Pro Asp Glu Glu Gly Ala Cys Gln Pro Cys Pro
1               5                   10                  15

Ile Asn Cys Thr His Ser Cys Val Asp Leu Asp Asp Lys Gly Cys Pro
            20                  25                  30

Ala Glu Gln Arg Ala Ser Pro Leu Thr Ser Ile Val Ser Ala Val Val
        35                  40                  45

Gly Ile Leu Leu Val Val Leu Gly Val Val Phe Gly Ile Leu Ile
    50                  55                  60

Lys Arg Arg Gln Gln Lys Ile Arg Lys Tyr Thr Met Arg Arg Leu Leu
65                  70                  75                  80

Gln Glu Thr Glu Leu Val Glu Pro Leu Thr Pro Ser Gly Ala Met Pro
                85                  90                  95

Asn Gln Ala Gln Met Arg Ile Leu Lys Glu Thr Glu Leu Arg Lys Val
            100                 105                 110

Lys Val Leu Gly Ser Gly Ala Phe Gly Thr Val Tyr Lys Gly Ile Trp
        115                 120                 125

Ile Pro Asp Gly Glu Asn Val Lys Ile Pro Val Ala Ile Lys Val Leu
    130                 135                 140
```

-continued

Arg Glu Asn Thr Ser Pro Lys Ala Asn Lys Glu Ile Leu Asp Glu Ala
145                 150                 155                 160

Tyr Val Met Ala Gly Val Gly Ser Pro Tyr Val Ser Arg Leu Leu Gly
                165                 170                 175

Ile Cys Leu Thr Ser Thr Val Gln Leu Val Thr Gln Leu Met Pro Tyr
            180                 185                 190

Gly Cys Leu Leu Asp His Val Arg Glu Asn Arg Gly Arg Leu Gly Ser
        195                 200                 205

Gln Asp Leu Leu Asn Trp Cys Met Gln Ile Ala Lys Gly Met Ser Tyr
    210                 215                 220

Leu Glu Asp Val Arg Leu Val His Arg Asp Leu Ala Ala Arg Asn Val
225                 230                 235                 240

Leu Val Lys Ser Pro Asn His Val Lys Ile Thr Asp Phe Gly Leu Ala
                245                 250                 255

Arg Leu Leu Asp Ile Asp Glu Thr Glu Tyr His Ala Asp Gly Gly Lys
                260                 265                 270

Val Pro Ile Lys Trp Met Ala Leu Glu Ser Ile Leu Arg Arg Arg Phe
            275                 280                 285

Thr His Gln Ser Asp Val Trp Ser Tyr Gly Val Thr Val Trp Glu Leu
        290                 295                 300

Met Thr Phe Gly Ala Lys Pro Tyr Asp Gly Ile Pro Ala Arg Glu Ile
305                 310                 315                 320

Pro Asp Leu Leu Glu Lys Gly Glu Arg Leu Pro Gln Pro Pro Ile Cys
                325                 330                 335

Thr Ile Asp Val Tyr Met Ile Met Val Lys Cys Trp Met Ile Asp Ser
                340                 345                 350

Glu Cys Arg Pro Arg Phe Arg Glu Leu Val Ser Glu Phe Ser Arg Met
            355                 360                 365

Ala Arg Asp Pro Gln Arg Phe Val Val Ile Gln Asn Glu Asp Leu Gly
        370                 375                 380

Pro Ala Ser Pro Leu Asp Ser Thr Phe Tyr Arg Ser Leu Leu Glu Asp
385                 390                 395                 400

Asp Asp Met Gly Asp Leu Val Asp Ala Glu Glu Tyr Leu Val Pro Gln
                405                 410                 415

Gln Gly Phe Phe Cys Pro Asp Pro Ala Pro Gly Ala Gly Gly Met Val
            420                 425                 430

His His Arg His Arg Ser Ser Ser Thr Arg Ser Gly Gly Gly Asp Leu
        435                 440                 445

Thr Leu Gly Leu Glu Pro Ser Glu Glu Glu Ala Pro Arg Ser Pro Leu
        450                 455                 460

Ala Pro Ser Glu Gly Ala Gly Ser Asp Val Phe Asp Gly Asp Leu Gly
465                 470                 475                 480

Met Gly Ala Ala Lys Gly Leu Gln Ser Leu Pro Thr His Asp Pro Ser
                485                 490                 495

Pro Leu Gln Arg Tyr Ser Glu Asp Pro Thr Val Pro Leu Pro Ser Glu
                500                 505                 510

Thr Asp Gly Tyr Val Ala Pro Leu Thr Cys Ser Pro Gln Pro Glu Tyr
            515                 520                 525

Val Asn Gln Pro Asp Val Arg Pro Gln Pro Pro Ser Pro Arg Glu Gly
        530                 535                 540

Pro Leu Pro Ala Ala Arg Pro Ala Gly Ala Thr Leu Glu Arg Ala Lys
545                 550                 555                 560

Thr Leu Ser Pro Gly Lys Asn Gly Val Val Lys Asp Val Phe Ala Phe
                565                 570                 575

```
Gly Gly Ala Val Glu Asn Pro Glu Tyr Leu Thr Pro Gln Gly Ala
                580                 585                 590

Ala Pro Gln Pro His Pro Pro Ala Phe Ser Pro Ala Phe Asp Asn
        595                 600                 605

Leu Tyr Tyr Trp Asp Gln Asp Pro Pro Glu Arg Gly Ala Pro Ser
    610                 615                 620

Thr Phe Lys Gly Thr Pro Thr Ala Glu Asn Pro Glu Tyr Leu Gly Leu
625                 630                 635                 640

Asp Val Pro Val

<210> SEQ ID NO 7
<211> LENGTH: 641
<212> TYPE: PRT
<213> ORGANISM: Homo sapiens

<400> SEQUENCE: 7

Met Phe Pro Asp Glu Glu Gly Ala Cys Gln Pro Cys Pro Ile Asn Cys
1               5                   10                  15

Thr His Ser Cys Val Asp Leu Asp Asp Lys Gly Cys Pro Ala Glu Gln
                20                  25                  30

Arg Ala Ser Pro Leu Thr Ser Ile Val Ser Ala Val Val Gly Ile Leu
            35                  40                  45

Leu Val Val Val Leu Gly Val Val Phe Gly Ile Leu Ile Lys Arg Arg
        50                  55                  60

Gln Gln Lys Ile Arg Lys Tyr Thr Met Arg Arg Leu Leu Gln Glu Thr
65                  70                  75                  80

Glu Leu Val Glu Pro Leu Thr Pro Ser Gly Ala Met Pro Asn Gln Ala
                85                  90                  95

Gln Met Arg Ile Leu Lys Glu Thr Glu Leu Arg Lys Val Lys Val Leu
            100                 105                 110

Gly Ser Gly Ala Phe Gly Thr Val Tyr Lys Gly Ile Trp Ile Pro Asp
        115                 120                 125

Gly Glu Asn Val Lys Ile Pro Val Ala Ile Lys Val Leu Arg Glu Asn
130                 135                 140

Thr Ser Pro Lys Ala Asn Lys Glu Ile Leu Asp Glu Ala Tyr Val Met
145                 150                 155                 160

Ala Gly Val Gly Ser Pro Tyr Val Ser Arg Leu Leu Gly Ile Cys Leu
                165                 170                 175

Thr Ser Thr Val Gln Leu Val Thr Gln Leu Met Pro Tyr Gly Cys Leu
            180                 185                 190

Leu Asp His Val Arg Glu Asn Arg Gly Arg Leu Gly Ser Gln Asp Leu
        195                 200                 205

Leu Asn Trp Cys Met Gln Ile Ala Lys Gly Met Ser Tyr Leu Glu Asp
210                 215                 220

Val Arg Leu Val His Arg Asp Leu Ala Ala Arg Asn Val Leu Val Lys
225                 230                 235                 240

Ser Pro Asn His Val Lys Ile Thr Asp Phe Gly Leu Ala Arg Leu Leu
                245                 250                 255

Asp Ile Asp Glu Thr Glu Tyr His Ala Asp Gly Gly Lys Val Pro Ile
            260                 265                 270

Lys Trp Met Ala Leu Glu Ser Ile Leu Arg Arg Arg Phe Thr His Gln
        275                 280                 285

Ser Asp Val Trp Ser Tyr Gly Val Thr Val Trp Glu Leu Met Thr Phe
290                 295                 300
```

```
Gly Ala Lys Pro Tyr Asp Gly Ile Pro Ala Arg Glu Ile Pro Asp Leu
305                 310                 315                 320

Leu Glu Lys Gly Glu Arg Leu Pro Gln Pro Pro Ile Cys Thr Ile Asp
                325                 330                 335

Val Tyr Met Ile Met Val Lys Cys Trp Met Ile Asp Ser Glu Cys Arg
                340                 345                 350

Pro Arg Phe Arg Glu Leu Val Ser Glu Phe Ser Arg Met Ala Arg Asp
            355                 360                 365

Pro Gln Arg Phe Val Val Ile Gln Asn Glu Asp Leu Gly Pro Ala Ser
        370                 375                 380

Pro Leu Asp Ser Thr Phe Tyr Arg Ser Leu Leu Glu Asp Asp Asp Met
385                 390                 395                 400

Gly Asp Leu Val Asp Ala Glu Glu Tyr Leu Val Pro Gln Gln Gly Phe
                405                 410                 415

Phe Cys Pro Asp Pro Ala Pro Gly Ala Gly Gly Met Val His His Arg
            420                 425                 430

His Arg Ser Ser Ser Thr Arg Ser Gly Gly Gly Asp Leu Thr Leu Gly
        435                 440                 445

Leu Glu Pro Ser Glu Glu Glu Ala Pro Arg Ser Pro Leu Ala Pro Ser
450                 455                 460

Glu Gly Ala Gly Ser Asp Val Phe Asp Gly Asp Leu Gly Met Gly Ala
465                 470                 475                 480

Ala Lys Gly Leu Gln Ser Leu Pro Thr His Asp Pro Ser Pro Leu Gln
                485                 490                 495

Arg Tyr Ser Glu Asp Pro Thr Val Pro Leu Pro Ser Glu Thr Asp Gly
            500                 505                 510

Tyr Val Ala Pro Leu Thr Cys Ser Pro Gln Pro Glu Tyr Val Asn Gln
        515                 520                 525

Pro Asp Val Arg Pro Gln Pro Pro Ser Pro Arg Glu Gly Pro Leu Pro
    530                 535                 540

Ala Ala Arg Pro Ala Gly Ala Thr Leu Glu Arg Ala Lys Thr Leu Ser
545                 550                 555                 560

Pro Gly Lys Asn Gly Val Val Lys Asp Val Phe Ala Phe Gly Gly Ala
                565                 570                 575

Val Glu Asn Pro Glu Tyr Leu Thr Pro Gln Gly Gly Ala Ala Pro Gln
            580                 585                 590

Pro His Pro Pro Pro Ala Phe Ser Pro Ala Phe Asp Asn Leu Tyr Tyr
        595                 600                 605

Trp Asp Gln Asp Pro Pro Glu Arg Gly Ala Pro Pro Ser Thr Phe Lys
    610                 615                 620

Gly Thr Pro Thr Ala Glu Asn Pro Glu Tyr Leu Gly Leu Asp Val Pro
625                 630                 635                 640

Val
```